(12) United States Patent
Yang

(10) Patent No.: US 10,369,125 B2
(45) Date of Patent: *Aug. 6, 2019

(54) METHOD OF TREATING RENAL SYSTEM DAMAGE

(71) Applicant: University of Utah Research Foundation, Salt Lake City, UT (US)

(72) Inventor: Tianxin Yang, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/492,732

(22) Filed: Apr. 20, 2017

(65) Prior Publication Data

US 2018/0092873 A1   Apr. 5, 2018

Related U.S. Application Data

(63) Continuation of application No. 13/944,453, filed on Jul. 17, 2013, now abandoned, which is a continuation-in-part of application No. 12/996,848, filed as application No. PCT/US2009/047825 on Jun. 18, 2009, now Pat. No. 8,686,038.

(60) Provisional application No. 61/073,945, filed on Jun. 19, 2008.

(51) Int. Cl.
  *A61K 31/704* (2006.01)
  *A61K 31/231* (2006.01)
  *A61K 45/06* (2006.01)
  *A61K 31/201* (2006.01)

(52) U.S. Cl.
  CPC .......... *A61K 31/201* (2013.01); *A61K 31/231* (2013.01); *A61K 31/704* (2013.01); *A61K 45/06* (2013.01)

(58) Field of Classification Search
  None
  See application file for complete search history.

(56) References Cited

U.S. PATENT DOCUMENTS

| | | | |
|---|---|---|---|
| 3,578,687 A | 5/1971 | Larkin et al. | |
| 3,819,561 A | 6/1974 | Bruenner | |
| 3,917,660 A | 11/1975 | Sasaki et al. | |
| 4,599,430 A | 7/1986 | Milberger et al. | |
| 5,412,137 A | 5/1995 | Prashad et al. | |
| 5,741,211 A | 4/1998 | Renirie et al. | |
| 6,187,747 B1 | 2/2001 | Singh et al. | |
| 6,262,029 B1 | 7/2001 | Press et al. | |
| 6,346,231 B1 | 2/2002 | Opheim | |
| 6,376,688 B1 | 4/2002 | Ferrante et al. | |
| 6,407,075 B1 | 6/2002 | Scott et al. | |
| 6,410,802 B1 | 6/2002 | Dasseux et al. | |
| 6,531,150 B1 | 3/2003 | Sunohara et al. | |
| 6,652,879 B2 | 11/2003 | Opheim | |
| 6,924,309 B2 | 8/2005 | Ferrante et al. | |
| 6,998,395 B2 | 2/2006 | Jackson et al. | |
| 7,312,191 B2 | 12/2007 | Rose et al. | |
| 7,452,907 B2 | 11/2008 | Cheng et al. | |
| 7,776,916 B2 | 8/2010 | Freeman et al. | |
| 7,977,315 B2 | 7/2011 | Rose et al. | |
| 8,309,526 B2 | 11/2012 | Freeman et al. | |
| 8,324,277 B2 | 12/2012 | Freeman | |
| 8,563,609 B2 | 10/2013 | Miller | |
| 8,686,038 B2 | 4/2014 | Yang | |
| 8,686,167 B2 | 4/2014 | Miller | |
| 8,735,449 B2 | 5/2014 | Freeman | |
| 8,933,255 B2 | 1/2015 | Miller | |
| 8,937,194 B2 | 1/2015 | Miller | |
| 9,006,473 B2 | 4/2015 | Freeman et al. | |
| 9,066,902 B2 | 6/2015 | Freeman et al. | |
| 9,186,408 B2 | 11/2015 | Freeman et al. | |
| 9,192,600 B2 | 11/2015 | Yang | |
| 9,271,952 B2 | 3/2016 | Cushing | |
| 9,295,678 B2 | 3/2016 | Freeman et al. | |
| 9,308,189 B2 | 4/2016 | Miller | |
| 9,585,855 B2 | 3/2017 | Yang | |
| 9,790,167 B2 | 10/2017 | Freeman et al. | |
| 2001/0037598 A1 | 11/2001 | Suppes et al. | |
| 2002/0128510 A1 | 9/2002 | Durley et al. | |
| 2003/0078299 A1 | 4/2003 | Ferrante et al. | |
| 2004/0006248 A1 | 1/2004 | Paiocchi et al. | |
| 2004/0092590 A1 | 5/2004 | Arterburn et al. | |
| 2004/0147599 A1 | 7/2004 | Gagnon et al. | |
| 2004/0176451 A1 | 9/2004 | Tamai et al. | |
| 2004/0254240 A1 | 12/2004 | Ferrante et al. | |
| 2005/0136103 A1 | 6/2005 | Ben-Sasson et al. | |

(Continued)

FOREIGN PATENT DOCUMENTS

| | | |
|---|---|---|
| EP | 1407767 | 4/2004 |
| EP | 1772149 | 4/2007 |

(Continued)

OTHER PUBLICATIONS

Cummings et al. in Journal of Pharmacology and Experimental Therapeutics 302(1), 8-17 (2002) (Year: 2002).*
Santos et al. in Archives of Toxicology 81:495-504 (2007) (Year: 2007).*
Gamesh et al. in Journal of Clinical Investigation 110:835-842 (2002) (Year: 2002).*
Abud-Mendoza et al., "Treating severe systemic lupus erythematosus with rituximab. An open study," Reumatol. Clin. 2009, vol. 5, No. 4, 147-152.
Adjei et al., "A Phase I Trial of the Farnesyl Transferase Inhibitor SCH66336: Evidence for Biological and Clinical Activity," Cancer Res. Apr. 1, 2000, vol. 60, 1871-1877.

(Continued)

*Primary Examiner* — Dennis Heyer
(74) *Attorney, Agent, or Firm* — Fenwick & West LLP

(57) ABSTRACT

Methods of treating the side effects of a toxic medical therapy using nitrated lipids are disclosed herein. In particular, the methods comprise the use of nitrated fatty acids or esters thereof to treat side effects, including organ system damage, caused by chemotherapy, radiotherapy, and the administration of other toxic agents.

5 Claims, 16 Drawing Sheets

(56) References Cited

U.S. PATENT DOCUMENTS

| | | |
|---|---|---|
| 2005/0232981 A1 | 10/2005 | Ben-Sasson |
| 2006/0018874 A1 | 1/2006 | Radhakrishnan et al. |
| 2006/0063953 A1 | 3/2006 | Maurizio et al. |
| 2006/0100278 A1 | 5/2006 | Cooper et al. |
| 2006/0241088 A1 | 10/2006 | Arterburn et al. |
| 2007/0232579 A1 | 10/2007 | Freeman et al. |
| 2007/0275893 A1 | 11/2007 | Quay |
| 2008/0096961 A1 | 4/2008 | Serhan et al. |
| 2009/0326070 A1 | 12/2009 | Freeman et al. |
| 2010/0166918 A1 | 7/2010 | Miller |
| 2010/0216884 A1 | 8/2010 | Freeman |
| 2010/0286257 A1 | 11/2010 | Perricone |
| 2010/0286271 A1 | 11/2010 | Perricone |
| 2010/0286272 A1 | 11/2010 | Perricone |
| 2010/0331268 A1 | 12/2010 | Freeman et al. |
| 2011/0082206 A1 | 4/2011 | Miller |
| 2011/0092594 A1 | 4/2011 | Yang |
| 2011/0196037 A1 | 8/2011 | Yang |
| 2011/0319325 A1 | 12/2011 | Miller |
| 2012/0136034 A1 | 5/2012 | Freeman et al. |
| 2013/0059912 A1 | 3/2013 | Freeman |
| 2013/0101514 A1 | 4/2013 | Cushing |
| 2013/0210917 A1 | 8/2013 | Freeman et al. |
| 2014/0024713 A1 | 1/2014 | Yang |
| 2014/0243380 A1 | 8/2014 | Yang |
| 2015/0018417 A1 | 1/2015 | Freeman et al. |
| 2015/0051283 A1 | 2/2015 | Dighiero et al. |
| 2015/0246059 A1 | 9/2015 | Freeman et al. |
| 2016/0081961 A1 | 3/2016 | Cushing |
| 2016/0151318 A1 | 6/2016 | Yang |
| 2016/0151391 A1 | 6/2016 | Freeman et al. |
| 2017/0095437 A1 | 4/2017 | Jorkasky |

FOREIGN PATENT DOCUMENTS

| | | |
|---|---|---|
| GB | 587992 | 5/1947 |
| GB | 1407932 | 10/1975 |
| JP | 62-132804 | 6/1987 |
| WO | WO 98/09621 | 3/1998 |
| WO | WO 01/06983 | 2/2001 |
| WO | WO 01/15673 | 3/2001 |
| WO | WO 01/21575 | 3/2001 |
| WO | WO 01/60778 | 8/2001 |
| WO | WO 01/78654 | 10/2001 |
| WO | WO 01/78719 | 10/2001 |
| WO | WO 01/79156 | 10/2001 |
| WO | WO 02/22559 | 3/2002 |
| WO | WO 02/102364 | 12/2002 |
| WO | WO 03/031399 | 4/2003 |
| WO | WO 03/039533 | 5/2003 |
| WO | WO 2005/073164 | 8/2005 |
| WO | WO 2005/110396 | 11/2005 |
| WO | WO 2006/055965 | 5/2006 |
| WO | WO 2006/086727 | 8/2006 |
| WO | WO 2007/140433 | 12/2007 |
| WO | WO 2008/008767 | 1/2008 |
| WO | WO 2008/011085 | 1/2008 |
| WO | WO 2008/103753 | 8/2008 |
| WO | WO 2009/017802 | 2/2009 |
| WO | WO 2009/038671 | 3/2009 |
| WO | WO 2009/129495 | 10/2009 |
| WO | WO 2009/134383 | 11/2009 |
| WO | WO 2009/149496 | 12/2009 |
| WO | WO 2009/155439 | 12/2009 |
| WO | WO 2010/042877 | 4/2010 |
| WO | WO 2010/078504 | 7/2010 |
| WO | WO 2010/129763 | 11/2010 |
| WO | WO 2010/129777 | 11/2010 |
| WO | WO 2011/011882 | 2/2011 |
| WO | WO 2011/014261 | 2/2011 |
| WO | WO 2011/098746 | 8/2011 |

OTHER PUBLICATIONS

Akaike et al., "Antagonistic Action of Imidazolineoxyl N-Oxides against Endothelium-Dreived Relaxing Factor/*NO through a Radical Reaction," Biochem. 1993, vol. 32, 827-832.

Alber, "Signaling mechanisms of the *Mycobacterium tuberculosis* receptor Ser/Thr protein kinases," Curr. Opin. Struct. Biol. Dec. 2009, vol. 19, No. 6, 650-657.

Altschul et al., "Gapped Blast and PSI-Blast: a new generation of protein database search programs," Nucleic Acids Res. 1997, vol. 25, No. 17, 3389-3402.

Anand et al., "Synthesis and Evaluation of Small Libraries of Triazolylmethoxy Chalcones, Flavanones and 2-aminopyrimidines as Inhibitors of Mycobacterial FAS-II and PknG," Bioorganic & Medicinal Chem. 2012, vol. 20, No. 17, 5150-5183.

Arnold et al., "Nitric oxide activates guanylate cyclase and increases guanosine 3':5'-cyclic monophosphate levels in various tissue preparations," Proc. Natl. Acad. Sci. 1977. vol. 74, 3203-3207.

Artim et al., "Nitro-oleic acid targets transient receptor potential (TRP) channels in capsaicin sensitive afferent nerves of rat urinary bladder," Expt. Neurol. 2011, vol. 232, 90-99.

Asakura et al., "Synthesis and biological evaluation of .gamma.-fluoro-.beta., .gamma.-unsaturated acids," J. of Flourine Chem. 2006, vol. 127, 800-808.

Baker et al., "Convergence of nitric oxide and lipid signaling: Anti-inflammatory nitro-fatty acids," Free Radic. Biol. Med. 2009, vol. 46, 989-1003.

Baker et al., "Fatty Acid Transduction of Nitric Oxide Signaling," The Journal of Biological Chemistry, 280(51):42464-42475, Dec. 23, 2005.

Baker et al., "Nitro-fatty Acid Reaction with Glutathione and Cysteine; Kinetic Analysis of Thiol Alkylation by a Michael Addition Reaction," J. of Biol. Chem. Oct. 19, 2007, vol. 282, No. 42, 31085-31093.

Baker et al., "Red cell membrane and plasma linoleic acid nitration products: Synthesis, clinical identification, and quantitation," Proc. Natl. Acad. Sci. Aug. 10, 2004, vol. 101, No. 32, 11577-11582.

Balazy et al., "Vicinal Nitrohydroxyeicosatrienoic Acids: Vasodilator Lipids Formed by Reaction of Nitrogen Dioxide with Arachidonic Acid," J. Pharmacol. ExTher. 2001, vol. 299, No. 2, 611-619.

Balazy, "Isomerization and Nitration of Arachidonic Acid by Nitrogen Dioxide," Advances in Mass Spectrometry 2001, vol. 15, 375-376.

Baldus et al., "Endothelial transcytosis of myeloperoxidase confers specificity to vascular ECM proteins as targets of tyrosine nitration," J. Clin. Invest. 2001, vol. 108, No. 12, 1759-1770.

Baldus et al., "Is NO News Bad News in Acute Respiratory Distress Syndrome," Am. J. Respir. Crit. Care Med. 2001, vol. 163, 308-310.

Ballini et al., "(Z)-7-Nitro-3-Heptene as Central Intermediate for the Synthesis of Jasmone, Methyl Jasmonate and .gamma.-Jasmolactone," Synthetic Communications 1989, vol. 19, Nos. 3-4, 575-583.

Ballini et al., "Fast Diastereoselective Baylis-Hillman Reaction by Nitroalkenes: Synthesis of Di- and Triene Derivatives," Tetrahedron 2004, vol. 60, 4995-4999.

Ballini et al., "Nitroalkanes and Ethyl Glyoxalate as Common Precursors for the Preparation of both .beta.-keto Esters and .alpha.,.beta.-unsaturated Esters," Tetrahedron Letters 2004, vol. 45, 7027-7029.

Banker et al., Modern Pharmaceutics, Marcel Dekker, Inc. 1979, New York (TOC).

Bates et al., "Nitroalkene Fatty Acids Mediate Activation of Nrf2/ARE-Dependent and PPAR.gamma.-Dependent Transcription by Distinct Signaling Pathways and with Significantly Different Potencies," Biochem. 2011, vol. 50, 7765-7773.

Bates et al., "Noncatalytic Interactions between Glutathione S-Transferases and Nitroalkene Fatty Acids Modulate Nitroalkene-Mediated Activation of Peroxisomal Proliferator-Activated Receptor .gamma.," Biochem. 2009, vol. 48, 4159-4169.

(56) References Cited

OTHER PUBLICATIONS

Batthyany et al., "Reversible Post-translational Modification of Proteins by Nitrated Fatty Acids In Vivo," J. Biol. Chem. Jul. 21, 2006, vol. 281, No. 29, 20450-20463.
Baumer, "Iodostarin 'Roche' in the treatment of Syphilis," Deutsche Medizinische Wochenschrift 1913, vol. 39, 1361 (case abstract) (1 page).
Beckman et al., "Apparent hydroxyl radical production by peroxynitrite: Implications for endothelial injury from nitric oxide and superoxide," Proc. Natl. Acad. Sci. 1990, vol. 87, 1620-1624.
Bell-Parikh et al., "Biosynthesis of 15-deoxy-.Delta..sup.12,14-PGJ.sub.2 and the ligation of PPAR.gamma.," J. Clin. Invest. 2003, vol. 112, No. 6, 945-955.
Bennett et al., Cecil Textbook of Medicine 1996, 20.sup.th Ed., vol. 1, 1004-1010.
Bervejillo et al., "Estudio del Potencial Anti-Aterogenico del AANO.sub.2 in Vivo," Tesina del grado de la Licenciatura en Bioquiica, Facultad de Ciencias, UdelR Feb. 2012, 5-6, Fig. 2 (in Spanish with English summary).
Biegert et al., "Sequence Context-specific Profiles for Homology Searching," PNAS 2009, vol. 106, No. 10, 3770-3775.
Bjorn, "Clues emerge about benefits of briefly blocking blood flow," Nature Feb. 2009, vol. 15, No. 2, 132.
Blair et al., "Bathophenanthrolinedisulphonic Acid and Bathocuproinedisulphonic Acid, Water Soluble Reagents for Iron and Copper," Talanta 1961, vol. 7, Nos. 3-4, 163-174 (abstract).
Blakemore, "The modified Julia olefination: alkene synthesis via the condensation of metallated heteroarylalkylsulfones with carbonyl compounds," J. Chem. Soc. Perkin Trans. I, Nov. 4, 2002, 2563-2585.
Blanco et al., "6-Methylnitroarachidonate: A novel esterified nitroalkene that potently inhibits platelet aggregation and exerts cGMP-mediated vascular relaxation," Free Radic. Biol. Med. 2011, vol. 50, 411-418.
Bligh et al., "A Rapid Method of Total Lipid Extraction and Purification," Can. J. Biochem. Physiol. 1959, vol. 37, No. 8, 911-917.
Bloodsworth et al., "Nitric Oxide Regulation of Free Radical- and Enzyme-Medicated Lipid and Lipoprotein Oxidation," Arterioscler. Thromb. Vasc. Biol. Jul. 2000, vol. 20, 1707-1715.
Boden et al., "Free fatty acids in obesity and type 2 diabetes: defining their role in the development of insulin resistance and .beta.-cell dysfunction," Euro. J. Clin. Invest. 2002, 32 (Suppl. 3), 14-23.
Bonacci et al., "Electrophilic Fatty Acids Regulate Matrix Metalloproteinase Activity and Expression," J. Biolo. Chem. 2011, vol. 286, No. 18, 16074-16081 (abstract).
Bonacci et al., "Gas-Phase Fragmentation Analysis of Nitro-Fatty Acids," J. Am. Soc. Mass Spec. 2011, vol. 22, 1534-1551.
Bonacci et al., "Nitro-oleic Acid Improves Insulin Signaling via Protein Tyrosine Phosphatase-1b Inhibition," Free Radical Bio. Med. Jan. 1, 2008, Elsevier Science, vol. 45, Suppl. 1, S154 (abstract).
Bonomi et al., "Direct Metal Ion Substitution at the [M(Scys).sub.4].sup.2 Site of Rubredoxin," J. Biol. Inorg. Chem. 1998, vol. 3, No. 6, 595-605.
Borniquel et al., "Nitrated oleic acid up-regulates PPAR.gamma. and attenuates experimental inflammatory bowel disease," Free Radic. Bio. Med. 2010, vol. 49, Iss. 4, 499-505.
Boruwa et al., "Catalytic Asymmetric Henry Reaction," Tetrahedron: Asymmetry Dec. 27, 2006, Report No. 90, 17, 3315-3326.
Burdge, ".alpha.-Linolenic Acid Metabolism in Men and Women: Nutritional and Biological Implications," Clin. Nutri. Metabol. Care 2004, vol. 7, 137-144.
Canadian Office Action dated Apr. 24, 2015, by the Canadian Patent Office corresponding Canadian Patent Application No. 2,729,053.
Cannon, Burger's Medicinal Chemistry and Drug Discovery 1995, Fifth Edition, vol. I: Principles and Practice, Chap. 19, John Wiley & Sons, Inc., 783-802.

Castro et al., "Cytochrome c: a catalyst and target of nitrate-hydrogen peroxide-dependent protein nitration," Arch. Biochem. Biophys. 2004, vol. 421, 99-107.
Chawla et al., "PPAR-.gamma. dependent and independent effects on macrophage-gene expression in lipid metabolism and inflammation," Nat. Med. 2001, vol. 7, No. 1, 48-52.
Chen et al., "Peroxisome Proliferator-Activated Receptors and the Cardiovascular System," Vitam. Horm. 2003, vol. 66, 157-188.
Chen et al., "Synthesis and Screening of Novel Vitamin E Derivatives for Anticancer Functions," European J. of Medicinal Chem. 2012, vol. 58, 72-83.
Chen et al., "Troglitazone Inhibits Aterhosclerosis in Apolipoprotein E-Knockout Mice: Pleiotropic Effects on CD36 Expression and HDL," Arterioscler. Thromb. Vasc. Biol. 2001, vol. 21, 372-377.
Clapp et al., "Oxygenation of Monounsaturated Fatty Acids by Soybean Liposygenase-1: Evidence for Transient Hydroperoxide Formation," Biochem. 2006, vol. 45, 15884-15892.
Claudel et al., "Reduction of atherosclerosis in apolipoprotein E knockout mice by activation of the retinoid X receptor," Proc. Natl. Acad. Sci. 2001, vol. 98, No. 5, 2610-2615.
Coffey et al., "Catalytic consumption of nitric oxide by 12/15-lipoxygenase: Inhibition of monocyte soluble guanylate cyclase activation," Proc. Natl. Acad. Sci. Jul. 3, 2001, vol. 98, No. 14, 8006-8011.
Cole et al., "Deciphering the Biology of *Mycobacterium tuberculosis* from the Complete Genome Sequence," Nature 1998, vol. 393, 537-544.
Cole et al., "Nitro-Fatty Acid Inhibition of Neointima Formation After Endoluminal Vessel Injury," Circ. Res. Nov. 6, 2009, 1-8; Suppl. Materials 1-6.
Coles et al., "Nitrolinoleate Inhibits Platelet Activation by Attenuating Calcium Mobilization and Inducing Phosphorylation of Vasodilator-stimulated Phosphoprotein through Elevation of cAMP," J. Biol. Chem. Feb. 22, 2002, vol. 277, No. 8, 5832-5840.
Coles et al., "Nitrolinoleate Inhibits Superoxide Generation, Degranulation, and Integrin Expression by Human Neutrophils. Novel Antiinflammatory Properties of Nitric Oxide-Derived Reactive Species in Vascular Cells," Circ. Res. Sep. 6, 2002, vol. 91, 375-381.
Collins et al., "Troglitazone Inhibits Formation of Early Atherosclerotic Lesions in Diabetic and Nondiabetic Low Density Lipoprotein Receptor-Deficient Mice," Arterioscler. Thromb. Vasc. Biol. 2001, vol. 21, 365-371.
Communication pursuant to Article 94(3) EPC for European Application No. 08 780 348.2-2123 dated Jul. 26, 2011.
Cosby et al., "Nitrite reduction to nitric oxide by deoxyhemoglobin vasodilates the human circulation," Nat. Med. 2003, vol. 9, No. 12, 1498-1505.
Cowley et al., "The *Mycobacterium tuberculosis* Protein Serine/threonine Kinase PknG is Linked to Cellular Glutamate/glutamine Levels and is Important for Growth In Vivo," Molecular Microbio. 2004, vol. 52, No. 6, 1691-1702.
Cui et al., "Nitrated Fatty Acids: Endogenous Anti-inflammatory Signaling Mediators," J. Biol. Chem. Nov. 24, 2006, vol. 281, No. 47, 35686-35698.
Dang et al. (Hung), "Anti-inflammatory Constituents of the Red Alga *Gracilaria verrucosa* and Their Synthetic Analogues," J. Nat. Prod. 2008, vol. 71, No. 2, 232-240.
Dangi et al., "Biogenic Synthesis, Purification, and Chemical Characterization of Anti-Inflammatory Resolvins Derived from Docosapentaenoic Acid (DPAn-6)," J. Biol. Chem. May 29, 2009, vol. 284, No. 22, 14744-14759.
Davies et al., "Oxidized Alkyl Phospholipids Are Specific, High Affinity Peroxisome Proliferator-activated Receptor .gamma. Ligands and Agonists," J. Biol. Chem. May 11, 2001, vol. 276, No. 19, 16015-16023.
De Meijere et al., "Metal-Catalyzed Cross-Coupling Reactions," Wiley-VCH Verlag GMbH & Co. 2004, Weinheim, vols. 1 and 2, XXII, ISBN-10: 3-527-30518-1 and ISBN-13: 978-3-527-30518-6 (TOC).
Defronzo et al., "Insulin Resistance: A Multifaceted Syndrome Responsible for NIDDM, Obesity, Hypertension, Dyslipidemia, and Atherosclerotic Cardiovascular Disease," Diabetes Care Mar. 1991, vol. 14, No. 3, 175-194.

(56) References Cited

OTHER PUBLICATIONS

Del Mar Grassa et al., "Daily Oral Oleoyl-estrone Gavage Induces a Dose-dependent Loss of Fat in Wistar Rats," Obesity Res. Mar. 1, 2001, vol. 9, No. 3, 202-209.
Delerive et al., "Oxidized Phospholipids Activated PPAR.alpha. in a Phospholipase A2-Dependent Manner," FEBS Lett. 2000, vol. 471, 34-38.
Dembitsky et al., "Natural halogenated fatty acids: their analogues and derivatives," Progress in Lipid Research 2002, vol. 41, No. 4, 315-367.
Denicola et al., "Diffusion of Nitric Oxide into Low Density Lipoprotein," J. Biol. Chem. 2002, vol. 277, No. 2, 932-936.
Denicola et al., "Diffusion of peroxynitrite across erythrocyte membranes," Proc. Natl. Acad. Sci. 1998, vol. 95, 3566-3571.
Desper et al., "Getting a Tree Fast: Neighbor Joining, FastME, and Distance-Based Methods," Curr. Protoc. Bioinformatics 2006, Chap. 6, Unit 6.3.
Diabetic ketoacidosis in www.mayoclinic.org/diseases-conditions/diabetic-ketoacidosis/basics/treat-ment/con-20026470 (retrieved from the internet Jan. 21, 2016).
d'Ischia et al., "Medium-dependent Competitive Pathways in the Reactions of Polyunsaturated Fatty Acids with Nitric Oxide in the Presence of Oxygen. Structural Characterisation of Nitration Products and a Theoretical Insight," Tetrahedron 1999, vol. 55, 9297-9308.
d'Ischia, "Oxygen-Dependent Nitration of Ethyl Linoleate with Nitric Oxide," Tetrahedron Lett. 1996, vol. 37, No. 32, 5773-5774.
Dodge et al., "Composition of phospholipids and of phospholipids fatty acids and aldehydes in human red cells," J. Lipid Res. 1967, vol. 8, 667-675.
Doksorubitsin-Ebeve, Instruksiya po primeneniyu lekarstvennogo perparata dlya meditinskogo primeneniya, Retrieved from the Internet: Nov. 19, 2014, http://medi.ru/doc/f4509.htm.
Dorwald, "Side reactions in Organic Synthesis," 2005, Wiley-VCH, 1-16.
Duan et al., "Nephrotoxicity of high- and low-osmolar contrast media: Protective role of forsinopril or telmisartan in a rat model," J. Central S. Univ. (Dec. 31, 2007), vol. 32, No. 5, 812-818.
Easton et al., "Polyunsaturated Nitroalkanes and Nitro-Substituted Fatty Acides," Synthesis 2001, vol. 3, 451-457.
Eberhardt et al., "Prevalence of Overweight and Obesity Among Adults with Diagnosed Diabetes—United States, 1988-1994 and 1999-2002," CDC, Nov. 19, 2004; vol. 53, No. 45, 1066-1068.
Eiserich et al., "Myeloperoxidase, a Leukocyte-Derived Vascular NO Oxidase," Sci. Jun. 28, 2002, vol. 296, 2391-2394.
Eiserich et al., "Pathophysiology of Nitric Oxide and Related Species: Free Radical Reactions and Modification of Biomolecules," Molec. Aspects Med. 1998, vol. 19, 221-357.
EP Communication issued on European Patent Application No. 09767748.8 dated Dec. 27, 2011.
Escudier et al., "Bevacizumab plus interferon alfa-2a for treatment of metastatic renal cell carcinoma: a randomized, double-blind phase III trial," The Lancet Dec. 22/29, 2007, vol. 370, 2103-2111.
European Examination Report issued in corresponding foreign application, EP Appl. 09767748.8, 1-3, dated Oct. 23, 2012.
Evans et al., "PPARs and the complex journey to obesity," Nat. Med. Apr. 2004, vol. 10, No. 4, 1-7.
European Office Action dated Jul. 9, 2013, by the European Patent Office, in Corresponding European Patent Application No. 09739186.6.
European Office Action dated Dec. 19, 2014, by the European Patent Office, in corresponding European Patent Application No. 09739186.6.
Extended European Search Report and Written Opinion issued in corresponding European Patent Application No. 12825790.4, 1-7 (dated Dec. 11, 2014).
Extended European Search Report and Written Opinion issued in corresponding European Patent Application No. 12839555.5, 1-6 (dated Feb. 2, 2015).
Extended European Search Report and Written Opinion issued in corresponding European Patent Application No. 16157509.7, 1-9 (dated May 30, 2016).
Extended European Search Report and Written Opinion issued in corresponding foreign application, EP 10821313.3, 1-9 (dated Jul. 2013).
Extended European Search Report and Written Opinion issued in corresponding foreign application, EP 11804082.3, 1-5 (dated Nov. 29, 2013).
Extended European Search Report and Written Opinion issued in EP Patent Application No. 09732031.1 dated Dec. 22, 2011.
Extended European Search Report and Written Opinion issued in EP Patent Application No. 13743207.6-1464, dated Jun. 22, 2015.
Extended European Search Report and Written Opinion issued in European Patent Application No. 09767748.8, 1-6, dated Dec. 8, 2011.
Feelisch et al., "Concomitant S-, N-, and heme-nitros(yl)ation in biological tissues and fluids: implications for the fate of NO in vivo," FASEB J. Nov. 2002, vol. 16, 1775-1785.
Ferreira et al., "Macrophage activation induces formation of the anti-inflammatory lipid cholesteryl-nitrolinoleate," Biochem. J. 2009, vol. 417, 223-234.
Ferry et al., "Binding of prostaglandins to human PPAR.gamma.: tool assessment and new natural ligands," Eur. J. Pharmacol. 2001, vol. 417, 77-89.
Finlayson-Pitts et al., "A Fourier Transform Infrared Spectrometry Study of the Reactions of Phosphatidylcholines with Gaseous $N_2O_5$ and $NO_2$," Toxicol. Appl. Pharmacol. 1987, vol. 89, 438-448.
Fiuza et al., "From the Characterization of the Four Serine/Threonine Protein Kinases (PknA/B/G/L) of Corynebacterium Glutamicum Toward the Role of PknA and PknB in Cell Division," J. Biolo. Chem. 2008, vol. 283, No. 26, 10899-18112.
Forman et al., "15-Deoxy-.Delta..sup.12-14-Prostaglandin $J_2$ is a Ligand for the Adipocyte Determination Factory PPAR.gamma.," Cell 1995, vol. 83, 803-812.
Freeman et al., "Nitro-fatty Acid Formation and Signaling," J. of Biol. Chem. Jun. 6, 2008, vol. 283, No. 23, 15515-15519.
Freshney, "Culture of Animal Cells," A Manual of Basic Technique 1983, Alan R. Liss, Inc., New York, 1-6.
Fu et al., "Oleylethanolamide regulates feeding and body weight through activation of the nuclear receptor PPAR-.alpha.," Nature Sep. 4, 2003, vol. 425, 90-93.
Furstner et al., "Total Synthesis of Epohelmin B and Its Analogues," Chem. Asian J. 2008, vol. 3, 310-318.
Gallon et al., "The Identification of the Allylic Nitrite and Nitro Derivatives of Methyl Linoleate and Methyl Linolenate by Negative Chemical Ionization Mass Spectroscopy," Lipids 1993, vol. 28, No. 2, 125-133.
Gallon et al., "The Reaction of Low Levels of Nitrogen Dioxide with Methyl Linoleate in the Presence and Absence of Oxygen," Lipids 1994, vol. 29, No. 3, 171-176.
Gavin III et al., "Reducing Cardiovascular Disease Risk in Patients with Type 2 Diabetes: A Message from the National Diabetes Education Program," Am. Fam. Physician Oct. 15, 2003, vol. 68, No. 8, 1569-74.
Gladwin et al., "Role of circulating nitrite and S-nitrosohemoglobin in the regulation of regional blood flow in humans," Proc. Natl. Acad. Sci. 2000, vol. 97, No. 21, 11482-11487.
Gladwin et al., "S-Nitrosohemoglobin Is Unstable in the Reductive Erythrocyte Environment and Lacks $O_2$/NO-linked Allosteric Function," J. Biol. Chem. 2002, vol. 277, No. 31, 27818-27828.
Gladwin et al., "The emerging biology of the nitrite anion," Nature Nov. 2005, vol. 1, No. 6, 308-314.
Glauser et al., "The inflammatory response and tissue damage. The example of renal scars following acute renal infection," Pediatric Nephrology Oct. 1987, vol. 1, No. 4, 615-622 (Abstract) (from PubMed website Jan. 22, 2016).
Goodman & Gilman's The Pharmacological Basis of Therapeutics, Ninth Edition 1996, McGraw-Hill Book Company, New York, Appendix II, 1707-1711 (TOC).
Goodman & Gilman's The Pharmacological Basis of Therapeutics, Sixth Edition 1980, MacMillan Publishing Co., New York (TOC).

(56) References Cited

OTHER PUBLICATIONS

Goodman & Gilman's The Pharmacological Basis of Therapeutics, Tenth Edition 2001, McGraw-Hill Book Company, New York (TOC).
Gorczynski et al., "Evaluation of Nitroalkenes as Nitric Oxide Donors," Bioorg. Med. Chem. Lett. 2007, vol. 17, 2013-2017.
Gorczynski et al., "Regio-and Stereospecific Synthesis and Nitric Oxide Donor Properties of .epsilon.-9- and .epsilon.-10-Nitrooctadec-9-enoic Acids," Org. Lett. Apr. 25, 2006, vol. 8, No. 11, 2305-2308.
Gregory et al., "5-HT.sub.3 Receptor Antogonists for the Prevention of Chemotherapy-Induced Nausea and Vomiting: A Comparison of Their Pharmacoogy and Clinical Efficacy," Drugs Feb. 1998, vol. 55, No. 2, 173-189.
Grisham, "Myoglobin-Catalyzed Hydrogen Peroxide Dependent Arachidonic Acid Peroxidation," Free Radic. Biol. Med. 1985, vol. 1, 227-232.
Groeger et al., "Cyclooxygenase-2 generates anti-inflammatory mediators from omega-3 fatty acids," Nat. Chem. Bio. Jun. 2010, vol. 6, 433-441.
Groeger et al., "Discovery, Structural Characterization and Quantification of Novel Inflammatory-Induced Electrophilic Fatty Acid Derivatives," Free Radical Bio. & Med. 2008, vol. 45, No. 1, S134.
Groeger et al., "Signaling Actions of Electrophiles: Anti-inflammatory Therapeutic Candidates," Molec. Interven. Feb. 2010, vol. 10, Issue 1, 39-50.
Guindon et al., "A Simple, Fast, and Accurate Algorithm to Estimate Large Phylogenies by Maximum Likelihood," Systematic Bio. 2003, vol. 52, No. 5, 696-704.
Guindon et al., "Estimating Maximum Likelihood Phylogenies with PhyML," Methods in Molecular Bio. 2009, vol. 537, 113-137.
Guo et al., "Atypical PKC.zeta. transduces electrophilic fatty acid signaling in pulmonary epithelial cells," Nitric Oxide 2011, vol. 25, 366-372.
Gutierrez et al., "Nitric Oxide Regulation of Superoxide-Dependent Lung Injury: Oxidant-Protective Actions of Endogenously Produced and Exogenously Administered Nitric Oxide," Free Radic. Biol. Med. 1996, vol. 21, No. 1, 43-52.
Hartmann et al., "A randomized trial comparing the nephrotoxicity of cisplatin/ifosfamide-based combination chemotherapy with or without amifostine in patients with solid tumors," Investigational New Drugs 2000, vol. 18, 281-289.
Hogg et al., "Inhibition of low-density lipoprotein oxidation by nitric oxide Potential role in atherogenesis," FEBS Lett. 1993, vol. 334, No. 2, 170-174.
Hogg et al., "Reactions of Nitric Oxide With Nitronyl Nitroxides and Oxygen: Prediction of Nitrate Formation by Kinetic Simulation," Free Radic. Res. 1995, vol. 22, No. 1, 47-56.
Hogg, "The Biochemistry and Physiology of S-nitrosothiols," Annu. Rev. Pharmacol. Toxicol. 2002, 42, 585-600.
Ichikawa et al., "Nitroalkenes Suppress Lipopolysaccharide-Induced Signal Transducer and Activator of Transcription Signaling in Macrophages: A Critical Role of Mitogen-Activated Protein Kinase Phosphatase 1," Endocrinology May 8, 2008, vol. 149, No. 8, 4086-4094.
Ignarro et al., "Endothelium-Derived Relaxing Factor From Pulmonary Artery and Vein Possesses Pharmacologic and Chemical Properties Identical to Those of Nitric Oxide Radical," Circ. Res. 1987, vol. 61, 866-879.
Ignarro et al., "Pharmacological Evidence that Endothelium-Derived Relaxing Factor is Nitric Oxide: Use of Pyrogallol and Superoxide Dismutase to Study Endothelium-Dependent and Nitric Oxide-Elicted Vascular Smooth Muscle Relaxation," J. Pharmacol. ExTher. 1988, vol. 244, No. 1, 181-189.
Iles et al., "Fatty acid transduction of nitric oxide signaling: nitrolinoleic acid mediates protective effects through regulation of the ERK pathway," Free Radic. Biol. Med. 2009, vol. 46, 866-875.
International Preliminary Report on Patentability for PCT/US2009/0047825 dated Jan. 6, 2011.
International Preliminary Report on Patentability issued in corresponding PCT/US2012/051304, 1-8 (dated Mar. 6, 2014).
International Preliminary Report on Patentability issued in corresponding PCT/US2012/059722, 1-9 (dated Apr. 24, 2014).
International Search Report and Written Opinion dated Dec. 4, 2009, in corresponding PCT/US2009/002628.
International Search Report and Written Opinion dated Apr. 21, 2015 corresponding to PCT/US2014/065203.
International Search Report and Written Opinion dated Aug. 19, 2013 corresponding to PCT/US2012/059722.
International Search Report and Written Opinion dated Jul. 13, 2011 corresponding to PCT/US2010/051059.
International Search Report and Written Opinion dated Jun. 2, 2013 corresponding to PCT/US2013/024476.
International Search Report and Written Opinion dated Jun. 30, 2009 corresponding to PCT/US2009/041018.
International Search Report and Written Opinion dated Mar. 23, 2012 corresponding to PCT/US2011/042011.
International Search Report and Written Opinion dated Mar. 5, 2010 corresponding to PCT/US2009/047825.
International Search Report and Written Opinion dated Nov. 1, 2012 corresponding to PCT/US2012/051304.
International Search Report and Written Opinion dated Nov. 27, 2014 corresponding to PCT/US2014/047073.
International Search Report and Written Opinion dated Oct. 12, 2006 corresponding to International Patent Application No. PCT/US2005/014305.
International Search Report for International Application No. PCT/US08/09274 dated Oct. 24, 2008.
International Search Report PCT/US2010/002141 dated Nov. 24, 2010.
Itoh et al., "Synthesis of Docosahexaenoic Acid Derivatives Designed as Novel PPAR.gamma. Agonists and Antidiabetic Agents," Bioorg. Med. Chem. 2006, vol. 14, 98-108.
Janero et al., "Differential nitros(yl)ation of blood and tissue constituents during glycerol trinitrate biotransformation in vivo," PNAS Nov. 30, 2004, vol. 101, No. 48, 16958-16963.
Japanese Office Action dated May 12, 2014, in Japanese Patent Application No. 2011-507440.
Japanese Office Action dated Oct. 15, 2013, in Japanese Patent Application No. 2011-507440.
Jeong et al., "Fenofibrate Prevents Obesity and Hypertriglyceridemia in Low-Density Lipoprotein Receptor-Null Mice," Metabolism May 2004, vol. 53, No. 5, 607-613.
Jimenez-Estrada et al., "Allyic Nitration of 3.beta.-Sitosterol and Cholesterol Acetate: Preparation of 7-Nitro Derivatives," Steroid Jun. 1997, vol. 62, 500-503.
Jourd'Heuil et al., "The Oxidative and Nitrosative Chemistry of the Nitric Oxide/Superoxide Reaction in the Presence of Bicarbonate," Arch. Biochem. Biophys. 1999, vol. 365, No. 1, 92-100.
Junping et al., "Pharmacokinetics and antitumor effects of vincristine carried microemulsions composed of PEG-lipid, oleic acid, vitamin E and cholesterol," Int. J. Pharm. Jan. 30, 2003, vol. 251, No. 1-2, 13-21, abstract provided.
Kansanen et al., "Nrf2-Dependent and -Independent Responses to Nitro-fatty Acids in Human Endothelial Cells: Identification of Heat Shock Response as the Major Pathway Activated by Nitro-oleic Acid," J. Biol. Chem. Oct. 5, 2009, 1-34.
Karp et al., "Clinical and Biologic Activity of the Farnesyltransferase Inhibitor R115777 in Adults with Refractory and Relapsed Acute Leukemias: A Phase 1 Clinical-Laboratory Correlative Trial," Blood Jun. 2001, vol. 97, No. 11, 3361-3369.
Katoh et al., "Recent Developments in the MAFFT Multiple Sequence Alignment Program," Briefings in Bioinformatics 2008, vol. 9, No. 4, 286-298.
Kelley et al., "Nitro-oleic Acid, a Novel and Irreversible Inhibitor of Xanthine Oxidoreductase," J. Biol. Chem. Dec. 28, 2008, vol. 283, No. 52, 36176-36184.
Khoo et al., "Activation of vascular endothelial nitric oxide synthase and heme oxygenase-1 expression by electrophilic nitro-fatty acids," Free Radic. Bio. Med. 2010, vol. 48, 230-239.
Khoo et al., "Electrophilic nitro-fatty acids: anti-inflammatory mediators in the vascular compartment," Curr. Opn. Pharml. 2010, vol. 10, 179-184.

(56) References Cited

OTHER PUBLICATIONS

Kim et al., "Bisubstrate Ketone Analogues as Serotonin N-Acetyltransferase Inhibitors," J. Med. Chem. 2001, vol. 44, No. 15, 2479-2485.

Kim et al., "The effect of PPAR-.gamma. agonist on glucose metabolism and insulin sensitivity in on-obese type 2 diabetic rat models," Diabetes, American Diabetes Association 55: Suppl. 1, Jun. 1, 2006.

Kissner et al., "Formation and Properties of Peroxynitrite as Studied by Laser Flash Photolysis, High-Pressure Stopped-Flow Technique, and Pulse Radiolysis," Chem. Res. Toxicol. Sep. 4, 1997, vol. 10, 1285-1292.

Kliewer et al. "A Prostaglandin J.sub.2 Metabolite Binds Peroxisome Proliferatory-Activated Receptor.gamma. and Promotes Adipocyte Differentiation," Cell 1995, vol. 83, 813-819.

Kliewer et al., "Fatty acids and eicosanoids regulate gene expression through direct interactions and peroxisome proliferator-activated receptors .alpha. and .gamma.," Proc. Natl. Acad. Sci. Apr. 1997, vol. 94, 4318-4323.

Kobayshi, "The Reaction of Nitrogen Dioxide with Lung Surface Components: The Reaction with cis-9-octadecenoic Acid," Chemosphere 1983, vol. 12, No. 9/10, 1317-1325.

Koenitzer et al., "Redox signaling in inflammation: interactions of endogenous electrophiles and mitochondria in cardiovascular disease," Ann. N.Y. Acad. Sci. 2010, vol. 1203, 45-52.

Kunin, "Urinary Tract Infections in Females," Clinical Infectious Diseases, Jan. 1994, vol. 18, 1-10.

Lai et al., "Reactions of Dinitrogen Pentoxide and Nitrogen Dioxide with 1-Palmitoy1-2-Oleoyl-sn-Glycero-3-Phosphocholine," Lipids 1991, vol. 26(4), 306-314. Abstract.

Larfars et al., "Activation of Nitric Oxide Release and Oxidative Metabolism by Leukotrienes B4, C4, and D4 in Human Polymorphonuclear Leukocytes," Blood Feb. 15, 1999, vol. 93, No. 4, 1399-1405.

Lee et al., "Peroxisome proliferators-activated receptor-.gamma. in macrophage lipid homeostasis," Trends Endocrinol. Metab. Oct. 2002, vol. 13, No. 8, 331-335.

Lee et al., "Rosiglitazone ameliorates cisplatin-induced renal injury in mice," Nephrol. Dial. Transplant. 2006, vol. 21, 2096-2105.

Levy et al., "Lipid mediator class switching during acute inflammation: signals in resolution," Nat. Immunol. Jul. 2001, vol. 2, No. 7, 612-619.

Li et al., "Differential inhibition of macrophage foam-cell formation and atherosclerosis in mice by PPARalpha, betta/delta, and gamma," J. Clin. Invest. 2004, vol. 114, No. 11, 1564-1576.

Li et al., "Molecular recognition of nitrated fatty acids by PPAR. gamma.," Nat. Struct. Mol. Biol. 2008, 1-3.

Li et al., "PPAR.alpha. Ligand Protects During Cisplatin-Induced Acute Renal Failure by Preventing Inhibition of Renal FAO and PDC Activity," Am. J. Physiol. Renal Physiol. Mar. 2004, vol. 286, F572-F580.

Lim et al., "Nitrolinoleate, a nitric oxide-derived mediator of cell function: Synthesis, characterization, and vasomotor activity," Proc. Natl. Acad. Sci. Dec. 10, 2002, vol. 99, No. 25, 15941-15946.

Lima et al., "Characterization of Linoleic Acid Nitration in Human Blood Plasma by Mass Spectrometry," Biochem. 2002, vol. 41, No. 34, 10717-10722.

Lima et al., "Cholesteryl Nitrolinoleate, a Nitrated Lipid Present in Human Blood Plasma and Lipoproteins," J. Lipid Res. 2003, vol. 44, 1660-1666.

Lima et al., "Nitrated Lipids Decompose to Nitric Oxide and Lipid Radicals and Cause Vasorelaxation," Free Radical Bio. Med. 2005, Elsevier Sciences, vol. 39, No. 4, 532-539.

Liu et al., "Accelerated reaction of nitric oxide with O.sub.2 within the hydrophobic interior of biological membranes," Proc. Natl. Acad. Sci. Mar. 1998, vol. 95, 2175-2179.

Liu et al., "Combined losartan and nitro-oleic acid remarkably improves diabetic nephrophaty in mice," Am. J. Physiol. Renal Physiol. Aug. 14, 2013, vol. 305, F1555-F1562.

Liu et al., "Nitrol-Oleic Acid Protects the Mouse Kidney from Ischemia and Reperfusion Injury," Am. J. Physiol. Renal Physiol. Oct. 2008, vol. 295, No. 4, F942-F949.

Lopez et al., "Second Generation of .alpha.-Tocopherol Analogs—Nitric Oxide Donors: Synthesis, Physiochemical, and Biological Characterization," Bioorg. Med. Chem. 2007, vol. 15, 6262-6272.

Loytynoja et al., "An Algorithm for Progressive Multiple Alignment of Sequences with Insertions," PNAS Jul. 26, 2005, vol. 102, No. 30, 10557-10562.

Lundberg et al., "Nitrate and nitrite in biology, nutrition and therapeutics," Nat. Chem. Bio. Dec. 2009, vol. 5, No. 12, 865-869.

Luzzio, "The Henry reaction: recent examples," Tetrahedron 2001, vol. 57, 915-945.

Ma et al., "Hydrohalogenation Reaction of Substituted 1, 2-Allenic Carboxylic Acids, Esters, Amides, Nitriles, and Diphenyl Phosphine Oxides," Synthesis Dec. 4, 2001, No. 5, 713-730.

Manini et al., "Chemistry of Nitrated lipids: Remarkable Instability of 9-Nitrolinoleic Acid in Neutral Aqueous Medium and a Novel Nitronitrate Ester Product by Concurrent Autoxidation/Nitric Oxide-Release Pathways," J. Org. Chem. (2008), vol. 73, No. 19, 7517-7525.

March, "Effects of Structure on Reactivity," Advanced Organic Chemistry (1977 edition), McGraw-Hill Book Company, New York, 251-259.

Marnett et al., "Regulation of Prostaglandin Biosynthesis by Nitric Oxide Is Revealed by Targeted Deletion of Inducible Nitric-oxide Synthese," J. Biol. Chem. 2000, vol. 275, No. 18, 13427-13430.

Marshall et al., "Nitrosation and oxidation in the regulation of gene expression," FASEB J. 2000, vol. 14, 1889-1900.

Marx et al., "Peroxisome Proliferator-Activated Receptors and Atherogenesis: Regulators of Gene Expression in Vascular Cells," Circulation Research, 94(9):1168-1178, May 14, 2004.

McIntyre et al., "Identification of an intracellular receptor for lysophosphatidic acid (LPA): LPA is a transcellular PPAR.gamma. agonist," Proc. Natl. Acad. Sci. 2003, vol. 100(1), 131-136.

McLean, "Iodostarin," Archives of Internal Medicine 1912, vol. 10, 509.

Menendez et al., "Effects of gama-linolenic acid and oleic acid on paclitaxel cytotoxicity in human breast cancer cells," European J. of Cancer (Oxford, England: 1990) Feb. 2001, vol. 37, No. 3, 402-213.

Messerschmidt et al., Handbook of Metalloproteins 2001, Hoboken, NJ, John Wiley & Sons, Inc. (abstract).

Metabolite definition at https://www.nlm.nih.gov/medlineplus/ency/article/002258.htm (retrieved from the internet Jan. 21, 2016).

Meyer et al., "Uremia," New Engl. J. Med. Sep. 27, 2007, vol. 357, 1316-1325.

Minghetti, "Cyclooxygenase-2 (COX-2) in Inflammatory and Degenerative Brain Diseases," J. Neuropathol. Exp. Neurol. Sep. 2004, vol. 63, No. 9, 901-910.

Miranda et al., "The Chemical Biology of Nitric Oxide," Nitric Oxide: Biology and Pathobiology 2000, Academic Press, San Diego, 41-55.

Mitschke et al., "9- and 10-Nitro-oleic acid do not interfere with the GC-MS quantitative determination of nitrate and nitrate in biological fluids when measured as their pentafluorobenzyl derivatives," Journal of Chromatography, 85(1):287-291, May 2007.

Montuschi et al., "Isoprostanes: markers and mediators of oxidative stress," FASEB J. Dec. 2004, vol. 18, 1791-1800.

Morgan et al., "Use of Animal Models of Human Disease for Nonclinical Safety Assessment of Novel Pharmaceuticals," Toxicol. Pathol. 2013, vol. 41, No. 3, 508-518.

Mukherjee et al., "A Selective Peroxisome Proliferator-Activated Receptor-.gamma. (PPAR.gamma.) Modulatory Blocks Adipocyte Differentiation byt Stimulates Glucose uptake in 3T3-L1 Adipocytes," Mol. Endocrinol. 2000, vol. 14, 1425-1433.

Nadtochiy et al. "Mitochondrial nitroalkene formation and mild uncoupling in ischaemic preconditioning: implications for cardioprotection," Card. Res. Adv. Access 2008, 1-8.

Nadtochiy et al., "Nitroalkenes Confer Acute Cardioprotection via Adenine Nucleotide Transloase 1," J. Biol. Chem. Jan. 27, 2012, vol. 287, No. 5, 3573-3580.

(56) References Cited

OTHER PUBLICATIONS

Nagano et al., "Use of tacrolimus, a potent antifibrotic agent, in bleomycin-induced lung fibrosis," Eur. Respir. J. 2006, vol. 27, 460-469.

Nagy et al., "Oxidized LDL Regulates Macrophage Gene Expression through Ligand Activation of PPAR.gamma.," Cell 1998, vol. 93, 229-240.

Napolitano et al., "Acid-Induced Structural Modifications of Unsaturated Fatty Acids and Phenolic Olive Oil Constituents by Nitrite Ions: A Chemical Assessment," Chem. Res. Toxicol. 2004, vol. 17, 1329-1337.

Napolitano et al., "Acid-Promoted Reactions of Ethyl Linoleate with Nitrite Ions: Formation and Structural Characterization of Isomeric Nitroalkene, Nitrohydroxy, and Novel 3-Nitro-1,5-hexadiene and 1,5-Dinitro-1,3-pentadiene Products," J. Org. Chem. 2000, vol. 65, No. 16, 4853-4860.

Napolitano et al., "The acid-promoted reaction of ethyl linoleate with nitrite. New insights from .sup.15N-labelling and peculiar reactivity of a model skipped diene," Tetrahedron 2002, vol. 58, 5061-5067.

Narayan et al., "Serine Threonine Protein Kinases of Mycobacterial Genus: Phylogeny to Function," Physiological Genomics 2007, vol. 29, 66-75.

Nathan, "Nitric oxide as a secretory product of mammalian cells," FASEB J. 1992, vol. 6, 3051-3064.

Newman et al., "Optimized Thiol Derivatizing Reagent for the Mass Spectral Analysis of Distributed Epoxy Fatty Acids," J. Chromato. May 22, 2011, No. 925, 223-240.

Niebisch et al., "Corynebacterial Protein Kinase G Controls 2-Oxoglutarate Dehydrogenase Activity via the Phosphorylation Status of the Odhl Protein," J. Biolo. Chem. 2006, vol. 281, No. 18, 12300-12307.

Notredame et al., "T-Coffee: A novel method for fast and accurate multiple sequence alignment," J. Molec. Bio. 2000, vol. 302, 205-217.

Nott et al., "An Intramolecular Switch Regulates Phosphoindependent FHA Domain Interactions in *Mycobacterium tuberculosis*," Sci. Signaling 2009, vol. 2, No. 63, ra 12.

O'Donnell et al., "15-Lipoxygenase Catalytically Consumes Nitric Oxide and Impairs Activation of Guanylae Cyclase," J. Biol. Chem. Jul. 16, 1999, vol. 274, No. 29, 20083-20091.

O'Donnell et al., "Catalytic Consumption of Nitric Oxide by Prostagladin H Synthase-1 Regulates Platelet Function," J. Biol. Chem. Dec. 8, 2000, vol. 275, No. 49, 38239-38244.

O'Donnell et al., "Interactions Between Nitric Oxide and Lipid Oxidation Pathways: Implications for Vascular Disease," Circ. Res. 2001, vol. 88, 12-21.

O'Donnell et al., "Nitration of Unsaturated Fatty Acids by Nitric Oxide-Derived Reactive Nitrogen Species Peroxynitrite, Nitrous Acid, Nitrogen Dioxide, and Nitronium Ion," Chem. Res. Toxicol. 1999, vol. 12, No. 1, 83-92.

O'Donnell et al., "Nitric Oxide Inhibition of Lipid Peroxidation: Kinetics of Reaction with Lipid Peroxyl Radicals and Comparison with .alpha.-Tocopherol," Biochem. 1997, vol. 36, No. 49, 15216-15223.

O'Hare et al., "Regulation of Glutamate Metabolism by Protein Kinases in Mycobacteria," Mol. Microbio. 2008, vol. 70, No. 6, 1408-1423.

Ono et al., "A Convenient Procedure for the Conversion .epsilon.-Nitroalkenes to (Z)-Nitroalkenes via erythro-.beta.-Nitroselenides," J. Chem. Soc., Chem Commun. 1987, 1550-1551.

Ortiz-Lombardia et al., "Crystal Structure of the Catalytic Domain of the PknB Serine/Threonine Kinase from *Mycobacterium tuberculosis*," J. Biolo. Chem. 2003, vol. 278, No. 15, 13094-13100.

Padmaja, "The Reaction of Nitric Oxide With Organic Peroxyl Radicals," Biochem. Biophys. Res. Commun. 1993, vol. 195, No. 2, 539-544.

Park et al., "Modulation of Tumor Necrosis Factor-Related Apoptosis-Inducing Ligand-Induced Apoptosis by Chemotherapy in Thyroid Cancer Cell Lines," Thyroid 2003, vol. 13. No. 12, 1103-1110.

Pawliczak et al., "85-kDa Cytosolic Phospholipase A.sub.2 Mediates Peroxisome Proliferator-activated Receptor .gamma. Activation in Human Lung Epithelial Cells," J. Biol. Chem. 2002, vol. 277, 33153-33163.

Pharma Medica (2002), 20(5):1999-210 (in Japanese with brief English relevance).

Pryor et al., "Reaction of Nitrogen Dioxide with Alkenes and Polyunsaturated Fatty Acids: Addition and Hydrogen Abstraction Mechanisms," J. Amer. Chem. Soc. 1982, vol. 104, 6685-6692.

Punchard et al., The Journal of Inflammation Editorial, Sep. 27, 2004, The Journal of Inflammation, BioMed Central, vol. 1, No. 1, 1-4.

Quijano et al., "Reaction of Peroxynitrite with Mn-Superoxide Dismutase: Role of the Metal Center in Decomposition Kinetics and Nitration," J. of Biol. Chem. Apr. 13, 2001, vol. 276, No. 15, 11631-11638.

Radi et al., "Peroxynitrite Oxidation of Sulfhydryls: The Cytotoxic Potential of Superoxide and Nitric Oxide," J. Biol. Chem. 1991, vol. 266, No. 7, 4244-4250.

Radi et al., "Peroxynitrite Reactions with Carbon Dioxide-Bicarbonate," Methods Enzymol. 1999, vol. 301, No. 37, 353-367.

Ranu et al., "Highly Selective Reduction of Conjugated Nitroalkenes with Zinc Borohydride in DME," Tetrahedron Letters 1991, vol. 32, No. 29, 3579-3582.

Rassaf et al., "Concomitant Presence of N-Nitroso and S-Nitroso Proteins in Human Plasma," Free Radic. Biol. Med. 2002, vol. 33, No. 11, 1590-1596.

Rassaf et al., "NO adducts in mammalian red blood cells: too much or too little?" Nat. Med. 2003, vol. 9, No. 5, 481-482.

Remington's Pharmaceutical Sciences 1990, 18th Ed. (TOC).

Rosen et al., "PPAR.gamma.: a Nuclear Regulator of Metabolism, Differentiation, and Cell Growth," J. Biol. Chem. 2001, vol. 276, No. 1, 37731-37734.

Rowe et al., "Acesulfame Potassium," Handbook of Pharma. Excipients 2006, 5.sup.th Ed., Great Britain: Pharmaceutical Press (abstract).

Rowe et al., Handbook of Pharma. Excipients 2006, 5.sup.th Ed., Great Britain: Pharmaceutical Press, American Pharmacists Association.

Rubbo et al., "Form on Nitric Oxide: Chemical Events in Toxicity. Nitrix Oxide Regulation of Tissue Free Radical Injury," Chem. Res. Toxicol. 1996, vol. 9, No. 5, 809-820.

Rubbo et al., "Nitric Oxide Inhibition of Lipoxygenase-Dependent Liposome and Low-Density Lipoprotein Oxidation: Termination of Radical Chain Propagation Reactions and Formation of Nitrogen-Containing Oxidized Lipid Derivatives," Arch. Biochem. Biophys. Dec. 1, 1995, vol. 324, No. 1, 15-25.

Rubbo et al., "Nitric Oxide Reaction with Lipid Peroxyl Radicals Spares .alpha.-Tocopherol during Lipid Peroxidation," J. Biol. Chem. 2000, vol. 275, No. 25, 10812-10818.

Rubbo et al., "Nitric Oxide Regulation of Superoxide and Peroxynitrite-dependent Lipid Peroxidation," J. Biol. Chem. Oct. 21, 1994, vol. 269, No. 42, 26066-26075.

Rudnick et al., "Contrast-induced nephropathy: How it develops, how to prevent it," Cleveland Clinic J. Med. Jan. 2006, vol. 73, No. 1, 75-87.

Rudolph et al., "Cardiovascular Consequences When Nitric Oxide and Lipid Signaling Converge," Circ. Res. Sep. 11, 2009, vol. 105, 511-522.

Rudolph et al., "Endogenous generation and protective effects of nitro-fatty acids in murine model of focal cardiac ischaemia and reperfusion," Cardiov. Res. Advance Access 2009, 1-12.

Rudolph et al., "Nitro-fatty Acid Metabolome: Saturation, Desaturation, .beta.-Oxidation, and Protein Adduction," J. Biol. Chem. Jan. 16, 2009, vol. 284, No. 3, 1461-1473.

Rudolph et al., "Nitro-Fatty Acids Reduce Atherosclerosis in Apolipoprotein E-Deficient Mice," Ather. Thromb. Vasc. Bio. May 2010, vol. 30, 938-945.

Rudolph et al., "Transduction of Redox Signaling by Electrophile-Protein Reactions," Sc. Signaling Sep. 29, 2009, vol. 2, Issue 90 re7, 1-13.

Ryan et al., "Diabetes and the Mediterranean diet: a beneficial effect of oleic acid on insulin sensitivity, adipocyte glucose transport and endothelium-dependent vasoreactivity," Q J Med, 93:85-91, 2000.

(56) References Cited

OTHER PUBLICATIONS

Saffer et al., "Choosing Drug Therapy for Patients with Hyperlipidemia," Am. Fam. Physic. Jun. 1, 2000, vol. 61, No. 11, 3371-3382.
Sarver et al., "Analysis of Peptides and Proteins Containing Nitrotyrosine by Matrix-assisted Laser Desorption/ionization Mass Spectrometry," J. Am. Soc. Mass Spectrom. 2001, vol. 12, No. 4, 439-448.
Satyanarayana et al., "Steroselective Synthesis of Diacids by the Nickel Cyanide and Phase-Transfer-Catalyzed Carbonylation of Alkynols. Novel Dependency of Product Stereochemistry and Optimum Stirring Speed on the Nature of the Phase-Transfer Agent," Organometallics 1991, vol. 10, 804-807.
Saulnier-Blache et al., "A simple and highly sensitive radioenzymatic assay for lysophosphatidic acid quantification," J. Lipid Res. 2000, vol. 41, 1947-1951.
Scarpini et al., "Treatment of Alzheimer's Disease: Current Status and New Perspectives," Lancet Neurol. Sep. 2003, vol. 2, 539-547.
Scherr et al., "Structural Basis for the Specific Inhibition of Protein Kinase G, a Virulence Factor of *Mycobacterium tuberculosis*," PNAS 2007, vol. 104, No. 29, 12151-12156.
Schopfer (Baker) et al., "Red cell membrane and plasma linoleic acid nitration products: Synthesis, clinical identification, and quantitation," Proc. Natl. Acad. Sci. Aug. 10, 2004, vol. 101, No. 32, 11577-11582.
Schopfer et al., "Covalent Peroxisome Proliferator-activated Receptor .gamma. Adduction by Nitro-fatty Acids: Selective ligand activity and anti-diabetic signaling actions," J. Biol. Chem. Apr. 16, 2010, vol. 285, No. 16, 12321-12333.
Schopfer et al., "Detection and quantification of protein adduction by electrophilic fatty acids: mitochondrial generation of fatty acid nitroalkene derivatives," Free Radic. Biol. Med. 2009, vol. 46, 1250-1259.
Schopfer et al., "Fatty Acid Transduction of Nitric Oxide Signaling. Nitrolinoleic Acid is a Hydrophobically Stabilized Nitric Oxide Donor," J. Biol. Chem. May 13, 2005, vol. 280, No. 19, 19289-19297.
Schopfer et al., "Nitrolinoleic Acid: An endogenous peroxisome proliferator-activated receptor .gamma. ligand," Proc. Natl. Acad. Sci. Feb. 15, 2005, vol. 102(7), 2340-2345.
Schopfer et al., "NO-dependent protein nitration: a cell signaling event or an oxidative inflammatory response?" Trends Biochem. Sci. 2003, vol. 28, 646-654.
Sculptoreanu et al., "Nitro-Oleic Acid Inhibits Firing and Activates TRPV-1 and TRPA1-Mediated Inward Currents in Dorsal Root Ganglion Neurons from Adult Male Rats," J. Pharm. Expt. Thera. 2010, vol. 333, No. 3, 883-895.
Serhan et al., "Anti-Inflammatory Actions of Neuroprotectin D1/Protectin D1 and Its Natural Stereoisomers: Assignments of Dihydroxy-Containing Docosatrienes," J. Immunology 2006, vol. 176, 1848-1859.
Setiadi et al., "Vitamin E models. Conformational analysis and stereochemistry of tetralin, choman, thiochroman and selenochroman," J. Molecular Structure (Theochem) 2002, vol. 594, 161-172.
Shaner et al., "Designing Herbicide Tolerance Based on Metabolic Alteration: the Challenges and the Future," In Pesticide Biotransformation in Plants and Microorganisms (Hall, J. et al.); ACS Symposium Series 2000, American Chemical Society; Washington DC.
Sharpless et al., "A Mild Procedure for the Conversion of Epoxides to Allylic Alcohols. The First Organoselenium Reagent," J. Am. Chem. Soc. Apr. 18, 1973, vol. 95, No. 8, 2697-2699.
Sieker et al., "Rubredoxin in Crystalline State," Methods Enzymol. 1994, vol. 243, 203-216.
Simopoulos et al., "Omega-3 Fatty Acids in Inflammation and Autoimmune Diseases," J. Amer. College of Nutrition 2002, vol. 21, No. 6, 495-505.
Smith, "Prostanoid biosynthesis and mechanisms of action," Am. Physiol. Soc. 1992, vol. 263, F181-F191.
Snider et al., "Oxidative and Dehydrative Cyclizations of Nitroacetate Esters with Mn(Oac).sub.3," Tetrahedron, Sep. 23, 2002, vol. 58, No. 39, 7821-7827.

Soding et al., "HHsenser: Exhaustive Transitive Profile Search Using HMM-HMM Comparison," Nucleic Acids Res. 2006, vol. 34, W374-378.
Strowig et al., "Combination therapy using metformin or thiazolidinediones and insulin in the treatment of diabetes mellitus," Diabetes, Obesity, and Metabolism 2005, vol. 7, 633-641.
Subczynski et al., "Permeability of Nitric Oxide through Lipid Bilayer Membranes," Free Radic. Res. 1996, vol. 24, 343-349.
Summons to Attend Oral Proceedings dated Oct. 2, 2012, from corresponding European Patent Application No. 08780348.
Supplementary European Search Report from European Application No. EP 08 78 0348 dated Jul. 30, 2010.
Szekely et al., "A Novel Drug Discovery Concept for Tuberculosis: Inhibition of Bacterial and Host Cell Signaling," Immun. Letters 2008, vol. 116, No. 2, 225-231.
Szoka et al., "Comparative Properties and Methods of Preparation of Lipid Vesicles (Liposomes)," Annu. Rev. Biophys. Bioeng. 1980, vol. 9, 467-508.
Tang et al., "Nitroalkenes induce rat aortic smooth muscle cell apoptosis via activation of caspase—dependent pathways," Biochem. Biophys. Res. Commun. 2010, vol. 397, 239-244.
Thatcher et al., "Nitrates and No Release: Contemporary Aspects in Biological and Medicinal Chemistry," Free Radic. Biol. Med. 2004, vol. 37, No. 8, 1122-1143.
Thomas et al., "The biological lifetime of nitric oxide. Implications for the perivascular dynamics of NO and O.sub.2," Proc. Natl. Acad. Sci. Jan. 2, 2001, vol. 98, No. 1, 355-360.
Tiwari et al., "Key Residues in *Mycobacterium tuberculosis* Protein Kinase G Play a Role in Regulating Kinase Activity and Survival in the Host," J. Biolol. Chem. 2009, vol. 284, No. 40, 27467-27479.
Tontonoz et al., "mPPAR.gamma.2: tissue-specific regulator of an adipocyte enhancer," Genes Dev. 1994, vol. 8, No. 10, 1224-1234.
Tontonoz et al., "Stimulation of Adipogenesis in Fibroblasts by PPAR.gamma.2, a Lipid-Activated Transcription Factor," Cell 1994, vol. 79, 1147-1156.
Toth, "High-Density Lipoprotein and Cardiovascular Risk," Circulation 2004, vol. 109, 1809-1812.
Trostchansky et al., "Nitrated Fatty Acids: Mechanisms of Formation, Chemical Characterization, and Biological Properties," Free Rad. Biol. Med. 2008, vol. 44, 1887-1896.
Tsikas et al., "Nitro-fatty Acids Occur in Human Plasma in the Picomolar Range: a Targeted Nitro-lipidomics GC-MS/MS Study," Lipids 2009, vol. 44, 855-865.
Tzameli et al., "Regulated Production of a Peroxisome Proliferatory-Activated Receptor-gamma Ligand during an Early Phase of Adipocyte Differentiation in 3T3-L1 Adipocytes," J. Biol. Chem. 2004, vol. 279, No. 34, 36093-36102.
Van Beilen et al., "Rubredoxins Involved in Alkane Oxidation," J. Biolol. Chem. 2002, vol. 184, No. 6, 1722-1732.
Vasil'Ev et al., "The action of nitrogen dioxide upon erucic acid," Lomonosova 1995, vol. 5, 50-58 (English abstract).
Vickers et al., "IGF-1 Treatment Reduces Hyperphagia, Obesity, and Hypertension in Metabolic Disorders Induced by Fetal Programming," Endocrinol. Sep. 2001, vol. 142, No. 9, 3964-3973.
Vidwans et al., "Differential Modulation of Prostaglandin H Synthase-2 by Nitric Oxide-Related Species in Intact Cells," Biochem. 2001, vol. 40, 11533-11542.
Villacorta et al., "Nitro-linoleic Acid Inhibits Vascular Smooth Muscle Cell Proliferation via the Keap1/Nrf2 Signaling Pathway," Am. J. Physiol. Heart Circ. Physiol. Apr. 27, 2007, 1-9.
Villacorta et al., "PPAR.gamma and its ligands: therapeutic implications in cardiovascular disease," Clin. Sci. 2009, vol. 116, 205-218.
Villarino et al., "Proteomic Identification of M. Tuberculosis Protein Kinase Substrates: PknB Recruits GarA, a FHA Domain-containing Protein, Through Activation Loop-mediated Interactions," J. Mol. Bio. 2005, vol. 350, No. 5, 953-963.
'Virtual Chembook' in www.elmhurst.edu/.about.chm/vchembook/551fattyacids.html (retrieved Dec. 12, 2012).
Von Knethen et al., "Activation of Peroxisome Proliferator-Activated Receptor .gamma. by Nitric Oxide in Monocytes/Macrophages Down-Regulates p47.sup.phox and Attenuates the Respiratory Burst," J. Immunol. 2002, vol. 169, 2619-2626.

(56) References Cited

OTHER PUBLICATIONS

Walburger et al., "Protein Kinase G from Pathogenic Mycobacteria Promotes Survival Within Macrophages," Sci. 2004, vol. 304, 1800-1804.
Wang et al., "Constitutive Activation of Peroxisome Proliferator-activated Receptor-.gamma. Suppresses Pro-inflammatory Adhesion Molecules in Human Vascular Endothelial Cells," J. Biol. Chem. 2002, vol. 277, No. 37, 34176-34181.
Wang et al., "Effects of Endogenous PPAR Agonist Nitro-Oleic Acid on Metabolic Syndrome in Obese Zucker Rats," PPAR Res. 2010, vol. 2010, 1-7.
Wang et al., "Nitro-oleic acid protects against endotoxin-induced endotoxemia and multiorgan injury in mice," Am. J. Physiol. Renal Physiol. 2010, vol. 298, F754-762.
Weber et al., "Fragmentation of Bovine Serum Albumin by Pepsin. 1. The Origin of the Acid Expansion of the Albumin Molecule," J. Biolo. Chem. 1964, vol. 239, No. 5, 1415-1423.
Wehenkel et al., "Mycobacterial Ser/Thr Protein Kinases and Phosphatases: Physiological Roles and Therapeutic Potential," Biochemica et biophysica acta 2008, vol. 1784, No. 1, 193-202.
Woodcock, "Synthesis of Nitrolipids. All Four Possible Diastereomers of Nitrooleic Acids: (E)- and (Z)-, 9- and 10-Nitro-octadec-9-enoic Acids," Organic Letters 2006, vol. 8, No. 18, 3931-3934.
Wright et al., "Fatty acid transduction of nitric oxide signaling: Nitrolinoleic acid potently activates endothelial heme oxygenase 1 expression," PNAS Mar. 14, 2006, vol. 103, No. 11, 4299-4304.
Wright et al., "Human Heme Oxygenase-1 Induction by Nitro-linoleic Acid is Mediated by cyclic AMP, AP-1, and E-box Response Element Interactions," Biochem. J. 2009, m. BJ20090339, 1-31.
Xu et al., "Lysophosphatidic Acid as a Potential Biomaker for Ovarian and Other Gynecologic Cancers," JAMA 1998, vol. 280, 719-723.
Zhang et al., "Lysophosphatidic Acid Induces Neointima Formation Through PPARgamma Activation," J. ExMed. 2004, vol. 199, No. 6, 763-774.
Zhang et al., "Nitro-Oleic Acid Inhibits Angiotensin II-Induced Hypertension," Circ. Res. 2010, vol. 107, 540-548.
Zhang et al., "Selective disruption of PPARgamma2 impairs the development of adipose tissue and insulin sensitivity," Proc. Natl. Acad. Sci. 2004, vol. 101, No. 29, 10703-10708.
Chinese First Office Action dated Feb. 25, 2013, in Chinese Application No. CN 00980125943.4.
Office Action dated Aug. 27, 2010, by the Japanese Patent Office in corresponding Japanese Patent Application No. 2014-186472, and a partial English Translation of the Office Action.
Office Action dated Mar. 16, 2012, for corresponding foreign application, Chinese Patent Application No. CN 200980123324.1 (English translation).
Office Action dated Oct. 21, 2011, for corresponding foreign application, Chinese Patent Application No. CN 200980127890.X (English translation).
Office Action dated Jul. 7, 2012, for corresponding foreign application, Chinese Patent Application No. CN 200980127890.X (English translation).
Office Action dated Apr. 1, 2013, for corresponding foreign application, Chinese Patent Application No. CN 200980127890.X (English translation).
Office Action dated Oct. 31, 2013, for corresponding foreign application, Chinese Patent Application No. CN 200980127890.X (English translation).
Office Action dated Jun. 5, 2014, for corresponding foreign application, Chinese Patent Application No. CN 200980127890.X (English translation).
Office Action dated May 5, 2014, for corresponding foreign application, CN2013100543 50.1 (English translation).
Office Action dated Nov. 21, 2013, for U.S. Appl. No. 13/387,489.
U.S. Appl. No. 13/646,985, Non-Final Office Action dated Jun. 12, 2014.
U.S. Appl. No. 13/646,985, Non-Final Office Action dated May 1, 2014.
U.S. Appl. No. 13/646,985, Notice of Allowance, dated Dec. 5, 2014.
U.S. Appl. No. 14/638,370, Non-Final Office Action, dated Jul. 8, 2015.
U.S. Appl. No. 14/638,370, Notice of Allowance, dated Nov. 18, 2015.

\* cited by examiner

METHOD OF TREATING RENAL SYSTEM DAMAGE

CROSS-REFERENCE TO RELATED APPPLICATIONS

The present application is a continuation of U.S. application Ser. No. 13/944,453, filed Jul. 17, 2013, which claims priority from and is a continuation-in-part from U.S. patent application Ser. No. 12/996,848, filed Mar. 4, 2011, which is a national phase application under 35 U.S.C. § 371 of International Application Serial No. PCT/US2009/047825, filed Jun. 18, 2009, which claims priority from U.S. Provisional Application Ser. No. 61/073,945, filed Jun. 19, 2008, all of which are herein incorporated by reference in their entireties.

STATEMENT OF GOVERNMENT RIGHTS

This invention was made with government support under Grant Numbers HL079453 and RO-1 DK 066592 awarded by the National Institutes of Health. The government has certain rights to this invention.

BACKGROUND

The present invention relates to methods of treating the side effects of a toxic medical therapy using nitrated lipids. In particular, the methods comprise the use of nitrated fatty acids or esters thereof to treat side effects, including organ system damage, caused by chemotherapy, radiotherapy, and the administration of other toxic agents.

Chemotherapy and radiotherapy provide an effective means of treating cancer. For example, cisplatin is among of the most successful anticancer drugs and is now being widely used for the treatment of testicular, head and neck, ovarian, cervical, nonsmall cell lung carcinoma, and many other types of cancer. In addition, approximately half of cancer patients received radiotherapy as a single and adjuvant therapy at some stage of their illness. However, a drawback of both chemotherapy and radiotherapy is the production of toxicity in normal tissues. For example, the clinical use of cisplatin is limited by its severe side effects, including neurotoxicity, ototoxicity, nausea and vomiting, hair loss, and nephrotoxicity. The mechanism of cisplatin-induced organ damage has been shown to be multifactorial, involving oxidative stress and apoptosis. Adriamycin is an anthracycline antibiotic and can cause severe side effects, including podocyte foot process effacement, increase glomerular permeability leading to proteinuria, and inflammation via oxygen free radicals. Other kinds of medical treatment may also involve administration of toxic agents, i.e., those that produce toxicity in normal tissues. Like chemotherapy and radiotherapy, the side effects associated with such treatments may limit the use of the treatment. The present invention attempts to solve these problems, as well as others.

SUMMARY OF THE INVENTION

In one aspect, methods and medicaments useful in the treatment of the side effects of toxic medical therapies are disclosed herein. The methods comprise administration of at least one nitrated lipid to a subject in need thereof in amounts effective to treat a side effect of a toxic medical therapy. In some embodiments of the present methods, the side effect is reduced relative to the side effect prior to administration of the nitrated fatty acid or ester thereof. The nitrated lipids may be used to prepare medicaments for treating a side effect of a toxic medical therapy.

A variety of nitrated lipids may be used in the present methods, including, e.g., nitrated fatty acids and esters thereof In some embodiments, the nitrated fatty acid is a monounsaturated fatty acid (e.g., oleic acid) or a polyunsaturated fatty acid. In illustrative embodiments, the oleic acid is selected from 9-nitrooleic acid, 10-nitrooleic acid, or combinations thereof Form the methods disclosed herein, a variety of lipids may be used to form the nitrated lipids, including, but not limited to a fatty acid or an ester thereof Similarly, a variety of fatty acids are compatible with the disclosed methods, including, but not limited to, monounsaturated and polyunsaturated fatty acids. Procedures for synthesizing nitrated lipids, sources for obtaining the lipids, and administration routes for the nitrated lipids are also provided.

The effective amount of the nitrated lipid administered to the subject may vary. In some aspects, the effective amount is that which prevents the subject from experiencing any of the disclosed side effects with any of the disclosed toxic medical therapies. In other aspects, the effective amount is an amount that reduces or eliminates the subject's side effects relative to the subject's side effects prior to administration of the nitrated lipid.

The methods disclosed herein may further comprise administrating a variety of therapeutic agents useful in the treatment of the underlying condition, disease, or disorder giving rise to any of the toxic medical therapies disclosed herein.

BRIEF DESCRIPTION OF THE DRAWINGS

In the accompanying figures, like elements are identified by like reference numerals among the several preferred embodiments of the present invention.

FIG. 7 is a bar graph of the ELISA analysis shows the levels of urinary albumin in different groups of mice at the indicated period of time after ADR injection. Control: n=8; ADR: n=18; ADR+OA-NO$_2$: n=16. Values are means±SE.

FIG. 8a is a bar graph of the ELISA analysis of plasma albumin in different groups of mice at day 8 after ADR injection. FIG. 8b is photographs of ascites in different groups of mice at day 8 after ADR injection. Control: n=8; ADR: n=18; ADR+OA-NO$_2$: n=16. Values are means ±SE.

FIG. 9a is a bar graph of the plasma triglyceride; FIG. 9b is a bar graph of the plasma creatinine; and FIG. 9c is a bar graph of the Blood Urea Nitrogen (BUN). Control: n=8; ADR: n=18; ADR+OA-NO$_2$: n=16. Values are means±SE.

FIG. 10a is representative micrographs showing kidney histology in different groups of mice at day 8 after ADR injection. Kidney sections were stained with periodic acid-Schiff reagent (magnification: right ×200, left ×1000 shown). FIGS. 10b-10c are bar graphs of the glomerulosclerosis index (GSI) and tubulointerstitial lesion index (TILI) in different groups of mice. Control: n=8; ADR: n=18; ADR+OA-NO$_2$: n=16. Values are means±SE.

FIG. 11a is an immunoblotting analysis of WT1 and β-actin in the kidneys. FIG. 11b is a bar graph of the densitometric analysis of WT1 protein. The densitometric value of WT1 protein was normalized by β-actin. FIG. 11c is a photograph of the immunohistochemical analysis of WT1 in the kidney. FIG. 11d is a bar graph of the number of WT1 positive cells per glomerulus. FIG. 11e is a bar graph of the qRT-PCR analysis of ZO-1 in the kidney. FIG. 11f is a bar graph of the qRT-PCR analysis of desmin. Control: n=8; ADR: n=18; ADR+OA-NO$_2$: n=16. Values are means±SE.

FIGS. 12a-12b are bar graphs of the qRT-PCR analysis of renal mRNA levels of FN and collage III. FIGS. 12c-12d are representative immunoblots of renal α-SMA and FN. β-actin served as a loading control. FIGS. 12e-12f are bar graphs of the densitometric analysis of immunoblots in C-D. FIGS. 12g-12h are bar graphs of the qRT-PCR analysis of renal mRNA levels of TGF-β and α-SMA. Control: n=8; ADR: n=18; ADR+OA-NO$_2$: n=16. Values are means±SE.

FIG. 13a is a bar graph of the measurement of plasma thiobarbituric acid-reactive substances (TBARS). FIG. 12b is a bar graph of the measurement of urinary TBARS. FIG. 13c is a bar graph of the measurement of kidney TBARS. Control: n=8; ADR: n=18; ADR+OA-NO$_2$: n=16. Values are means±SE.

FIGS. 14a-14b are bar graphs of the qRT-PCR analysis of renal mRNA expression of p47$^{phox}$ and gp91$^{phox}$. FIGS. 14c-14d are representative immunoblots and bar graphs of the densitometric of gp91$^{phox}$ and β-actin in the kidneys. The densitometric value of gp91$^{phox}$ protein was normalized by β-actin. Control: n=8; ADR: n=18; ADR+OA-NO$_2$: n=16. Values are means±SE.

DETAILED DESCRIPTION OF THE INVENTION

Figure 1:
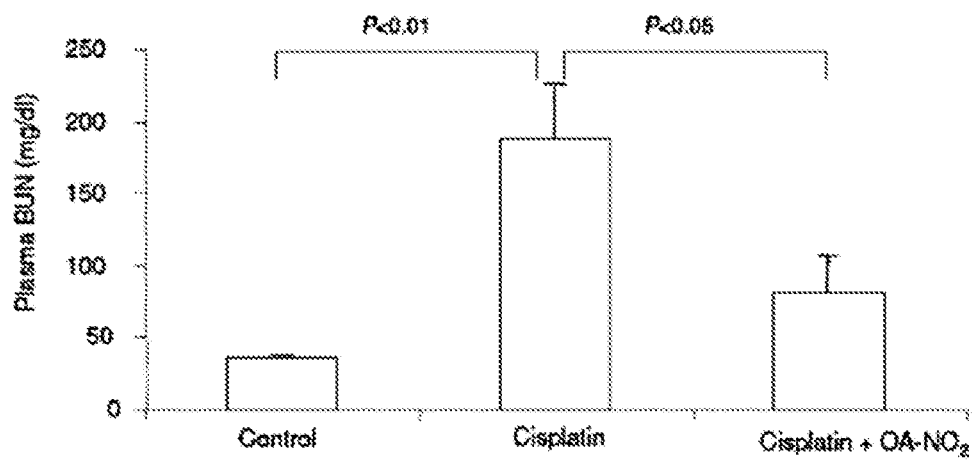
FIG. 1. A bar graph showing the plasma concentrations of Blood Urea Nitrogen (BUN) in mice under the conditions indicated. N=5-6. Data are mean±n SE. B6129S2/J mice (male, 3-4-mo-old) received vehicle (Control) or a single i.p. injection of cisplatin alone (20 mg/kg in saline). After 20 min, the cisplatin group was randomly divided to receive an i.p injection of OA-NO$_2$ (400 mg/kg in ethanol) or an equivalent amount of ethanol at 6-h intervals for 48 h. The results show that nitrated fatty acid OA-NO$_2$ improves renal function in a mouse model of cisplatin-induced toxicity.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The following terms are used throughout as defined below.

"Treat" means to alleviate, in whole or in part, symptoms associated with a condition or disorder (e.g., disease), or halt of further progression or worsening of those symptoms, or prevention or prophylaxis of the condition or disorder. Similarly, as used herein, an "effective amount" of a compound disclosed herein refers to an amount of the compound that alleviates, in whole or in part, symptoms associated with a condition or disorder, or halts further progression or worsening of those symptoms, or prevents or provides prophylaxis for the disease or disorder. For example, in treating a side effect of a toxic medical treatment, the prevention of, reduction of, or elimination of the side effect are examples of desirable treatment results. Finally, treating does not necessarily occur by administration of one dose of the compound, but often occurs upon administration of a series of doses. Thus, an effective amount, an amount sufficient to alleviate, or an amount sufficient to treat a disease, disorder, or condition may be administered in one or more administrations. "Pretreatment" means to deliver or administer an effective amount of the compound prior to a subject being exposed to a toxic medical therapy. In one embodiment, pretreatment may be between 1-3 hours before a toxic medical therapy, alternatively between 1-3 days before a toxic medical therapy. Posttreatement may be any time after a subject being exposed to a toxic medical therapy.

The methods disclosed herein comprise administration of a nitrated lipid. Nitrated lipids are lipids comprising at least one nitro (NO$_2$) group covalently bonded to the lipid. The methods disclosed herein encompass administration of a single type of nitrated lipid or a mixture of two or more different types of nitrated lipids. By way of example, one type of nitrated lipid is 9-nitro-9-cis-octadecenoic acid. Thus, "type" identifies the compound by lipid, stereochemistry, and number and position of NO$_2$ groups.

Nitrated lipids include nitrated fatty acids or esters thereof. A fatty acid is a substituted or unsubstituted alkyl or alkenyl having a terminal COOH group. In some embodiments, the alkyl or alkenyl is a C$_8$-C$_{24}$ alkyl or alkenyl. A wide variety of fatty acids may be used, including, but not limited to monounsaturated fatty acids and polyunsaturated fatty acids. In some embodiments, the monounsaturated fatty acid is oleic acid. In some embodiments, the oleic acid is 9-nitrooleic acid, 10-nitrooleic acid, or combinations thereof. An ester of a fatty acid is a substituted or unsubstituted alkyl or alkenyl having a terminal COOR group. In some embodiments, the alkyl or alkenyl is a $C_8$-$C_{24}$ alkyl or alkenyl. R may include, but is not limited to, a $C_{1-8}$ alkyl or glyceryl.

Nitrated lipids and its derivatives may be synthesized according to known procedures. For example, U.S. Patent Publication No. 2007/0232579 (incorporated herein by reference in its entirety) discloses a procedure comprising the steps of reacting a lipid with a mercuric salt, a selenium compound, and a nitrating compound to produce a first intermediate and reacting the first intermediate with an oxidant. Useful mercuric salts, selenium compounds, nitrating compounds, oxidants, relative amounts of reactants, and reaction conditions are also disclosed in U.S. Patent Publication No. 2007/0232579. Such synthetic procedures may provide mixtures of two or more types of nitrated lipids which may be separated or purified by techniques known in the art, if desired. Nitrated lipids, its derivatives, and other lipids may be synthesized according to other procedures as demonstrated in U.S. Patent Publication Nos. 2009/326070, 2009/326070, 2012/0136034, 2011/0082206, and (incorporated herein by reference in their entireties)

The lipids described above may be obtained from a variety of sources. For example, lipids may be commercially available or may be obtained from natural sources. Plant oils, including, but not limited to olive oil, linseed oil, flaxseed oil, rapeseed oil, and perilla oil are possible natural sources of fatty acid lipids. Fish oils or other marine oils are other possible sources of fatty acids. Nitrated lipids present in any of these or other natural sources may be extracted and/or purified for use in the methods disclosed herein.

The disclosed methods involve treatment or pretreatment of a side effect of a toxic medical therapy. A variety of side effects may be treated, including, but not limited to organ system damage, nausea, vomiting, and hair loss. By organ system, it is meant a group of related organs. By way of example only, the urinary system is an organ system including the kidneys, the ureters, the bladder, and the urethra. Other examples of organ systems include, but are not limited to, the digestive system, the nervous system, the auditory system, the circulatory system, the endocrine system, the excretory system, the skeletal system, the respiratory system, the reproductive system, the muscular system, the lymphatic system, immune system, integumentary system, and the integumentary system. "Organ system damage" refers to damage to one or more of the organs making up the organ system as a result of a toxic medical therapy. Organ damage may include, but is not limited to, oxidative stress to the organ, cytotoxicity, and necrosis or apoptosis of organ cells. Other organ damage may include Cardiotoxicity (heart damage), Hepatotoxicity (liver damage), Nephrotoxicity (kidney damage), Ototoxicity (damage to the inner ear), producing vertigo, Encephalopathy (brain dysfunction), Immunosuppression and myelosuppression, typhlitis, infertility, immunodepression, tendency to bleed, gasointestinal distress, and the like.

These examples of organ damage and others may be readily identified using well-known pathological techniques. By way of example only, kidney damage may be identified by examining the overall renal morphology, the dilation of renal tubules, and the appearance of protein cast. Organ damage may also be identified by measuring certain biomarkers of organ damage in a subject. Useful biomarkers include, but are not limited to biological substances or activities that provide a marker of organ dysfunction, oxidative stress, necrosis or apoptosis. By way of example only, a biomarker of organ dysfunction includes, but is not limited to the rise of plasma creatinine and BUN for renal dysfunction, and the rise of serum aspartate aminotransferase (AST) and alanine aminotransferase (ALT) for hepatic dysfunction. Biomarkers of oxidative stress include, but are not limited to, the NADPH oxidase subunits $p47^{phox}$ and $gp91^{phox}$, and thiobarbituric acid-reactive substances (TBARS). Biomarkers of inflammation include, but are not limited to, Tumor necrosis factor (TNF-α), Interleukin 1 (IL-1β) and monocyte chemotactic protein-1 (MCP-1). A biomarker of apoptosis includes, but is not limited to, the activity of caspase 3, 6, and 9, NF-κB, peroxisome proliferator-activated receptors (PPARs). Another biomarker of organ damage is myeloperoxidase, MPO. An increase in the level of MPO, BUN, AST, ALT, TBARS, $p47^{phox}$, or $gp91^{phox}$ in a subject or an increase in the activity of caspase 3, 6, and 9 in the subject may provide an indication of organ damage. Other organ system damage that may be recovered by the nitrated lipids may be found in Wang et al. "Nitro-oleic acid protects against endotoxin-induced endotoxemia and multiorgan injury in mice", AJP- Renal Physiol. 298(3): F754-F762 (2010).

The disclosed methods encompass a variety of toxic medical therapies. By toxic medical therapy it is meant a medical therapy that involves administration of an agent that is capable of producing toxicity in normal tissues. The agent may be chemical or physical. Chemical agents include, but are not limited to, alkylating agents, anti-metabolites, alkaloids and terpenes, topoisomerase inhibitors, antibiotics, monoclonal antibodies, tyrosine kinase inhibitors, nanoparticles, and hormones. Examples of antibiotics include, but are not limited to, actinomycin, anthracyclines, and other cytotoxic antibiotics. Anthracyclines include, but are not limited to, doxorubicin (Adriamycin), daunorubicin, valrubicin, idarubicin, epirubicin, which also inhibit topoisomerase II. Cytotoxic antibiotics include, but are not limited to, bleomycin, plicamycin, mitomycin. Bleomycin acts in a unique way through oxidation of a DNA-bleomycin-Fe(II) complex and forming free radicals, which induce damage and chromosomal aberrations.

Examples of alkylating agents include, but are not limited to, cisplatin, mechlorethamine, cyclophosphamide, chlorambucil, carboplatin, ifosfamide, and oxaliplatin. Examples of anti-metabolites include, but are not limited to azathioprine, mercaptopurine, and other purine and pyrimidine analogues. Examples of alkaloids and terpenes include, but are not limited to, vinca alkaloids, etoposide, teniposide, paclitaxel, taxanes, podophyllotoxins, and docetaxel. Examples of vinca alkaloids include, but are not limited to, vincristine, vinblastine, vinorelbine, and vindesine Examples of topoisomerase inhibitors include, but are not limited to, irinotecan, topotecan, etoposide, etoposide phosphate, teniposide, semisynthetic derivatives of epipodophyllotoxins, and amsacrine. Examples of monoclonal antibodies include, but are not limited to, trastuzumab, cetuximab, rituximab, and bevacizumab. Examples of hormones include, but are not limited to, steroids such as dexamethasone, finasteride, aromatase inhibitors, tamoxifen, and goserelin. Other examples of chemical agents include, but are not limited to, contrast agents, NSAIDS, COX-2 inhibitors, ACE inhibitors, ARBs, and lithium. An example of a physical agent includes, but is not limited to, radiation. By way of example only, the radiation may be ionizing radiation, proton therapy, electrochemotherapy, or laser radiation.

In the disclosed methods, the nitrated lipids are administered to a subject in an effective amount. An effective amount is an amount that 1) prevents the subject from experiencing any of the disclosed side effects associated with any of the disclosed toxic medical therapies; 2) reduces the subject's side effects relative to the subject's side effects prior to administration of the nitrated lipid; and/or eliminates the subject's side effects relative to the subject's side effects prior to administration of the nitrated lipid. By way of example only, in some embodiments, the side effect is urinary system damage comprising damage to one or more kidneys. In this illustrative example, the effective amount is an amount that prevents, reduces, or eliminates the damage to the kidneys. The damage to the kidneys may include, but is not limited to, any of the types of damage described above.

In one embodiment, the nitrated lipids act as a signaling molecule capable of activating peroxisome proliferator-activated receptors (PPARs), inhibiting nuclear factor kappa-light-chain-enhancer of activated B cells (NF-κB), and releasing Nitrous Oxide (NO) in response to at least one toxic medical therapy. In one embodiment, in response to a toxic medical therapy, the nitrated lipids may attenuate glomerulosclerosis, podocyte loss, and tubulointerstitial fibrosis. In one embodiment, in response to a toxic medical therapy, the nitrated lipids reduce oxidative stress including plasma and urinary TBARS, reduce expression of NAD(P)H oxidase p47$^{phox}$ and gp91$^{phox}$, and suppress inflammation including expression of TNF-α, IL-1β and MCP-1 in response to a toxic medical therapy. In one embodiment, the nitrated lipids exert a renoprotective action against toxic medical therapies via anti-inflammatory and anti-oxidant properties, as supported by the examples below. All three PPAR subtypes α, δ, and γ, share anti-inflammatory and antioxidant properties, they may protect against renal I/R injury via different mechanisms. PPARα provided protection likely via activation of fatty acid β-oxidation, a mechanism that also appeared to protect against cisplatin-induced nephrotoxicity, while PPARδ may act via activation of the PKB/Akt pathway, leading to the increased spread of renal tubular epithelial cells. The nitrated lipids activate all three PPAR subtypes to provide anti-inflammatory protection against toxic medical therapies.

In another embodiment, the mechanism of action of the nitrated lipids in response to a toxic medical therapy protects podocytes and prevents albuminuria, hypoalbuminemia, hyperlipidemia and ascites. Podocytes play a crucial role in regulation of glomerular function. Injury to podocytes can disrupt the structural and functional integrity of the slit diaphragm leading to proteinuria. WT1 is a pivotal transcription factor that is essential for the maintenance of the differentiated features of adult podocytes. In response to a toxic medical therapy, nitrated lipids significantly preserve the expression of WT1 proteins and prevent downregulation of WT1 proteins. In another embodiment, nitrated lipids reverse the mRNA reduction of epithelial marker ZO-1 and the mRNA increase of the Mesenchymal marker desmin in response to a toxic medical therapy. Tight junction protein ZO-1 is a protein that in humans is encoded by the TJP1 gene. ZO-1 is a protein located on a cytoplasmic membrane surface of intercellular tight junctions. The encoded protein may be involved in signal transduction at cell-cell junctions. Desmin is a protein that in humans is encoded by the DES gene. Desmin is a type III intermediate filament found near the Z line in sarcomeres. Desmin is a 52kD protein that is a subunit of intermediate filaments in skeletal muscle tissue, smooth muscle tissue, and cardiac muscle tissue. In another embodiment, in response to a medical therapy, the nitrated lipids ameliorate glomeruloseclerosis, alleviate the accumulation of mesangial matrix, attenuate the prominent tubular dilation, reduce the intraluminal protein casts, improve the narrow Bowman's capsule, and attenuate of albuminuria.

In one embodiment, pretreatment with nitrated lipids before the administration of a toxic medical therapy ameliorates albuminuria concomitantly with a reduction of plasma thiobarbituric acid-reactive substances (TBARS) levels. NADPH oxidase system is a major superoxide-generating system contributing to ROS generation in Chronic Kidney Disease (CKD) including nephropathy in response to a toxic medical therapy. Nitrated lipids significantly attenuate ADR-induced up-regulation of NADPH oxidase subunit gp91$^{phox}$ and p47$^{phox}$ at both mRNA and protein levels; gp91$^{phox}$ and p47$^{phox}$ are of particular importance as the former contains the catalytic domain and the latter is necessary for cytosolic subunit translocation and for initiation of NADPH oxidase assembly in kidney. Nitrated lipids include an antioxidant property by suppressing NADPH oxidase expression to account for the renoprotective action in a pretreatment step before administration of a toxic medical therapy.

Inflammation is an important component of pathophysiology of toxic medical therapies, such as ADR nephropathy. Tubulointerstitial inflammation with infiltration of T and B lymphocytes and macrophages occurs in response to a toxic medical therapy, such as ADR. Macrophages play a pivotal role in the disease process of ADR nephropathy and other immunosuppressive actions of toxic medical therapies. Excessive renal production of proinflammatory cytokines Tumor necrosis factor (TNF-α), Interleukin 1 (IL-1β) and monocyte chemotactic protein-1 (MCP-1) in the early stages of ADR nephropathy. In one embodiment, administration of nitrated lipids significantly inhibits the induction of the proinflammatory cytokines Tumor necrosis factor (TNF-α), Interleukin 1 (IL-1β) and monocyte chemotactic protein-1 (MCP-1) in response to a toxic medical therapy. Nitrated lipids attenuate the endotoxin-elicited inflammatory response via diverse mechanisms involving activation of mitogen-activated protein kinase phosphatase 1 and nitroalkylation of NF-κB p65 in response to a toxic medical therapy. Moreover, nitrated lipids have anti-inflammatory and renoprotective action in endotoxin-induced endotoxemia in response to a toxic medical therapy as to amerliorate the production of proinflammatory cytokines (i.e., TNF-α and IL-1β) and adhesion molecules (i.e., ICAM1), which may involve not only neutrophils but also other inflammatory cells such as macrophages and lymphocytes.

As is understood by those of skill in the art, specific effective amounts of the nitrated lipids to be administered will vary depending upon a variety of factors, e.g., the condition to be treated, the age, body weight, general health, sex, and diet of the subject, the dose intervals, and the administration route. In some embodiments, the effective amount of the nitrated lipid ranges from about 1 μg per day to about 1 g per day, from about 1 mg per day to about 500 mg per day, from about 1 mg per day to about 100 mg per day, or from about 2 mg per day to about 10 mg per day.

Any of the nitrated lipids disclosed herein may be administered to the subject alone or in combination with one or more other therapeutic agents. By "administered in combination," it is meant that the nitrated lipids and the therapeutic agents may be administered as a single composition, simultaneously as separate doses, or sequentially. Sequential administration refers to administering the nitrated lipids and at least one therapeutic agent either before or after the other. A variety of therapeutic agents may be used, including, but not limited to, those useful in the treatment of the underlying condition, disease, or disorder giving rise to any of the toxic medical therapies disclosed herein.

The nitrated lipids may be administered to a subject via any number of pharmaceutical formulations and administration routes. The formulations can take the form of granules, powders, tablets, capsules, syrup, suppositories, injections, emulsions, elixirs, suspensions or solutions. These formulations may further include a variety of well-known pharmaceutically acceptable additives, carriers, and/or excipients as necessary. The formulations may be delivered to the subject by various routes of administration, e.g., by topical administration, transdermal administration, oral administration, by nasal administration, rectal administration, subcutaneous injection, intravenous injection, intramuscular injection, or intraperitoneal injection. Any of the formulations, delivery methods, and pharmaceutically acceptable additives, carriers, and excipients disclosed in U.S. Patent Publication No. 2007/0232579 may also be used with the methods described herein. Another possible route of administration includes incorporating the nitrated lipid into various food products. Food products, include, but are not limited to butter, margarine, vegetable oils, and the like.

The subjects of the disclosed methods include any animal that can benefit from the administration of a nitrated lipid. In some embodiments, the subject is a mammal, e.g., a human, a primate, a dog, a cat, a horse, a cow, a pig, or a rodent, e.g., a rat or mouse. Typically, the mammal is a human. In some aspects, the subject is undergoing or has undergone any of the disclosed toxic medical therapies. Such subjects may or may not actually be experiencing any of the disclosed side effects. In other aspects, the subject has not yet undergone the toxic medical therapy, but is susceptible to any of the disclosed side effects because of an imminent toxic medical therapy.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

For the purposes of this disclosure and unless otherwise specified, "a" or "an" means "one or more."

The present invention, thus generally described, will be understood more readily by reference to the following examples, which are provided by way of illustration and are not intended to be limiting of the present invention.

EXAMPLES

Materials and Methods
Animals.
Male 3-4-month-old B6129SF2/J mice were from Jackson Laboratories (Bar Harbor, Me.). All animals were housed in an air-conditioned room with a 12-hour light/dark cycle. All procedures and protocols were in accordance with guidelines set by the Laboratory Animal Care Committee at the University of Utah.
Materials.
9-Nitrooleic acid and 10-nitrooleic acid are two regioisomers of nitrooleic acid ($OA-NO_2$), which are formed by nitration of oleic acid in approximately equal proportions in vivo. The two compounds were purchased from Cayman Chemicals (Ann Arbor, Mich.) (9-nitrooleic acid: Cat#10008042; 10-nitrooleic acid: Cat #10008043) and used as an 1:1 mixture of the isomers.
Protocols for Animal Experiments.
Protocol for testing effects of $OA-NO_2$ on cisplatin-induced toxicity in B6129SF2/J mice. B6129S2/J mice (male, 3-4-mo-old) received vehicle (saline) or a single i.p. (intraperitoneal) injection of cisplatin alone (20 mg/kg in saline). After 20 minutes, the cisplatin group was randomly divided to receive an i.p injection of $OA-NO_2$ (400 mg/kg in ethanol) or an equivalent amount of ethanol at 6-hour intervals for 48 hours. The control group also received an i.p. injection of the equivalent amount of ethanol at the same frequencies. At the end of the experiments, under isoflurane anesthesia, blood was withdrawn from the vena cava using 1 cc insulin syringe and kidneys were harvested for analysis of morphology and gene expression.

Example 1

Figure 2:
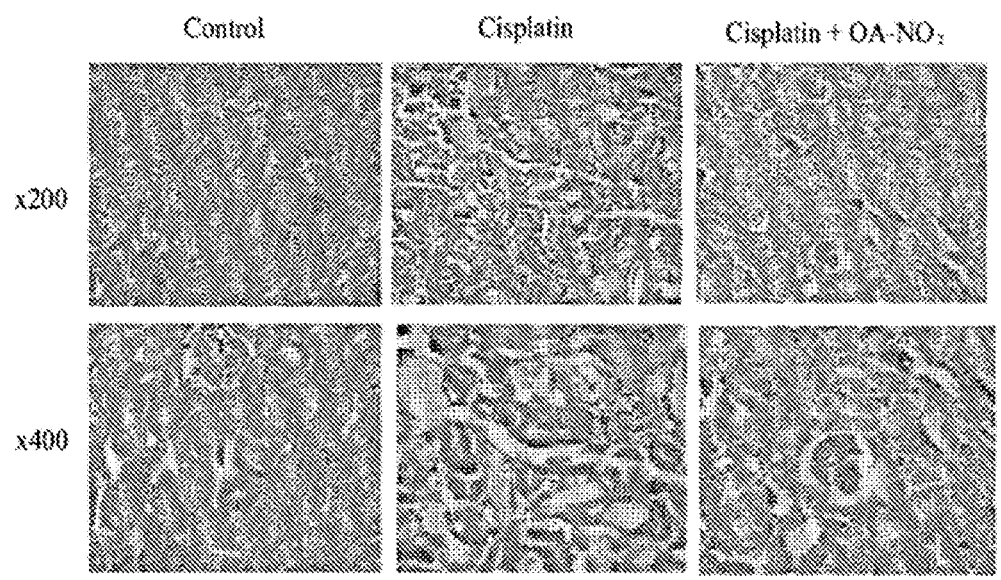
FIG. 2. The nitrated fatty acid OA-NO$_2$ improves renal morphology in a mouse model of cisplatin-induced toxicity. Shown are representative images of renal morphology at ×200 and ×400 magnifications.
Figure 3:
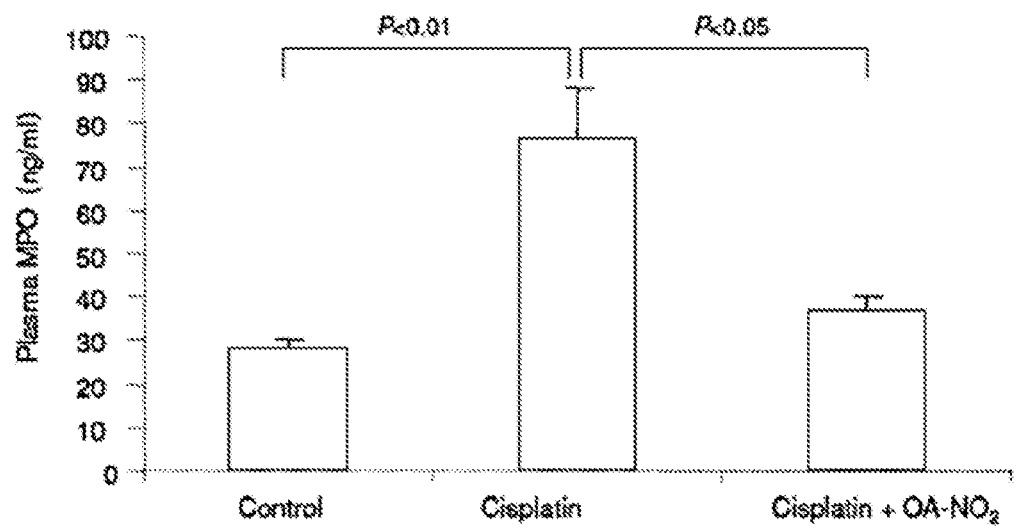
FIG. 3. A bar graph shows the nitrated fatty acid OA-NO$_2$ reduces plasma myeloperoxidase (MPO) in cisplatin treated mice. MPO concentrations are determined by EIA. N=5-6. Data are mean±SE.
Figure 4:
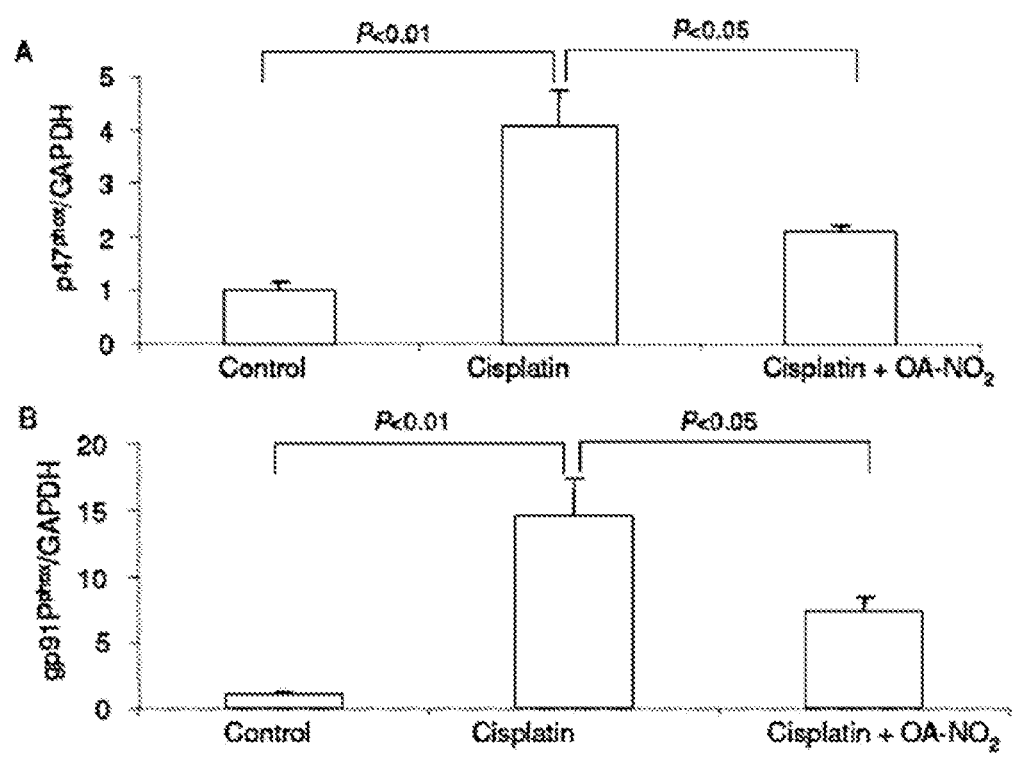
FIG. 4. Bar graphs of real time RT-PCR analysis of p47$^{phox}$ (A), gp91$^{phox}$ (B) in control mice and mice treated with cisplatin alone or in combination with OA-NO$_2$. N=5-6 in each group. Data are mean±SE.
Figure 5:
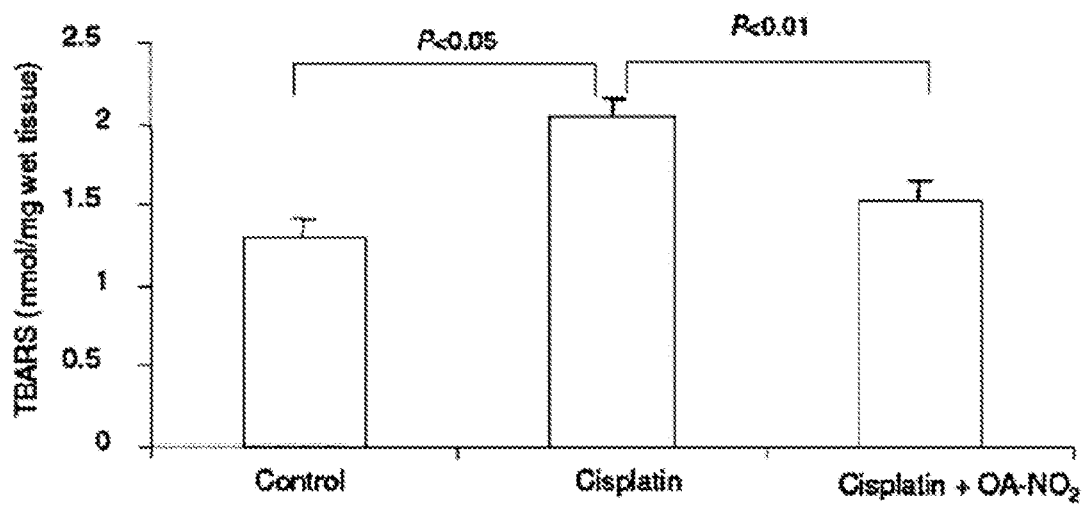
FIG. 5. A bar graph shows kidney TBARS in control mice and mice treated with cisplatin alone or in combination with OA-NO$_2$. N=5-6 in each group. Data are mean±SE.
Figure 6:
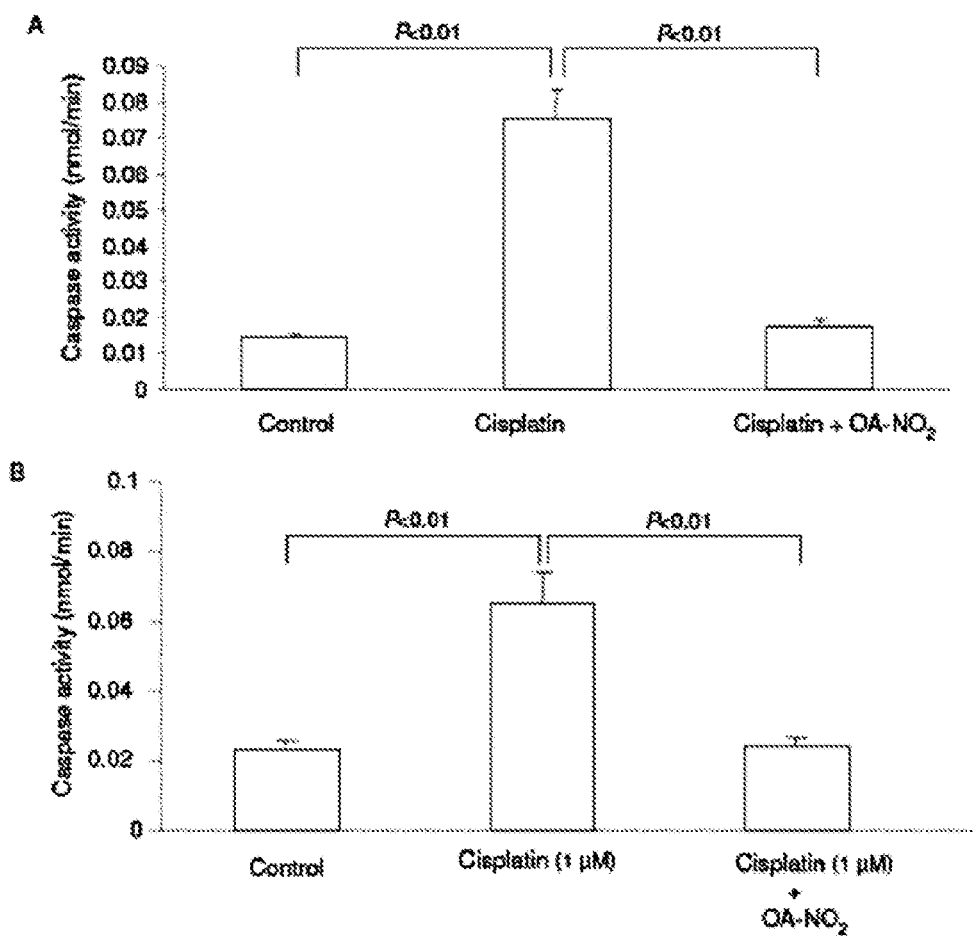
FIG. 6. Bar graphs show the effects of nitrated fatty acid OA-NO$_2$ on cisplatin-induced apoptosis in vivo and in vitro. A), Caspase activity in the mouse kidney. N=5-6 in each group. B), Caspase activity in cultured human proximal tubular cells (HK2). Following pretreatment for 1 h with vehicle or 1.5 µM OA-NO$_2$, the cells were exposed for 24 h to 1 µM cisplatin. N=3 in each group. Data are mean±SE.
Figure 7:
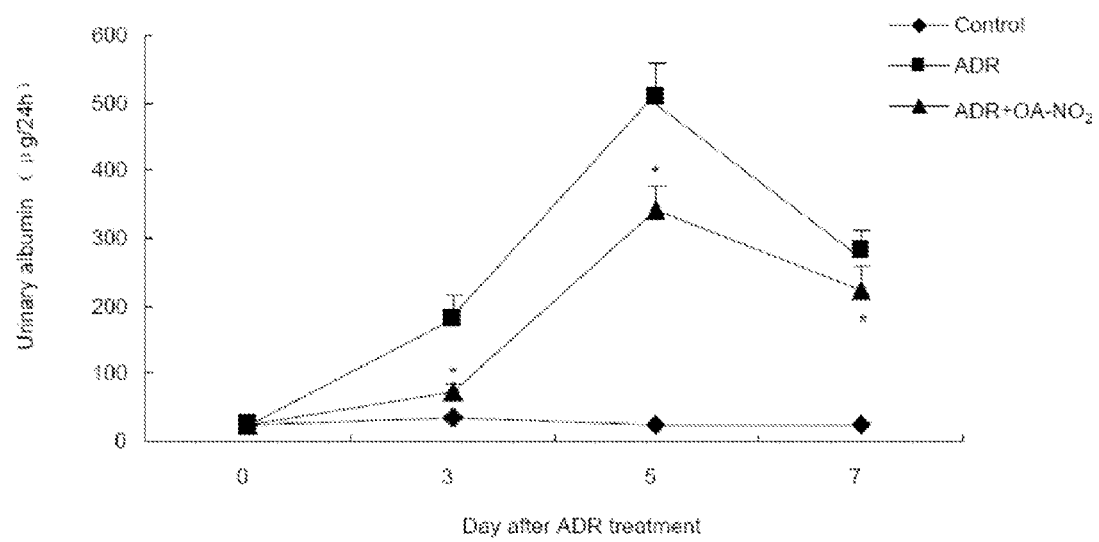
FIG. 7. Nitrated fatty acid OA-NO$_2$ ameliorates albuminuria in Adriamycin (ADR) nephropathy.

Evaluation of the Therapeutic Potential for Using Nitrated Fatty Acid $OA-NO_2$ in Managing Chemotherapy-Related Toxicity A single dose of i.p. injection of cisplatin induced renal dysfunction as indicated by the marked rise in plasma BUN (FIG. 1), accompanied by severe renal histological abnormalities characterized by distortion of the overall renal morphology, dilation of renal tubules, and appearance of protein cast (FIG. 2). In a sharp contrast, posttreatment with $OA-NO_2$ markedly attenuated these functional and pathological changes (FIGS. 1-2). Cisplatin treatment induced increases in plasma level of MPO (marker of neutrophil infiltration) (FIG. 3), kidney expression of NADPH oxidase subunits $p47^{phox}$ and $gp91^{phox}$ (major superoxide generating enzyme) (FIG. 4), kidney thiobarbituric acid-reactive substances (TBARS, index of oxidative stress) (FIG. 5), and activity of caspase (index of apoptosis) (FIG. 6A), all of which were attenuated or completely corrected by $OA-NO_2$. In cultured human proximal tubular cells (HK2), exposure to 1.0 µM cisplatin induced a 3-fold increase in caspase activity that was almost completely normalized by $OA-NO_2$ (FIG. 6B).

Materials and Methods
Animals and treatments
Male BABL/C mice were purchased from the Jackson Laboratories (Bar Harbor, Me., USA). Mice were maintained in a temperature-controlled barrier facility with a 12:12-h light-dark cycle and were given free access to standard laboratory chow and tap water. Mice were randomized into three groups: 1) control, 2) Adriamycin (ADR), and 3) ADR+nitro-oleic acid ($OA-NO_2$). In Group 3, $OA-NO_2$ (dissolved in ethanol) was administered at 5 mg/kg/day via subcutaneously implanted osmotic mini-pump and vehicle (ethanol) was given to the other two groups. This dose was chosen based a previous study (35). After 2 days of pretreatment with OA-NO$_2$, Groups 2 and 3 received a single tail vein injection of ADR at 10 mg/kg. Group 1 received a single tail vein injection of saline. Twenty four-hour urine was collected with using metabolic cages. Seven days after ADR treatment, all mice were killed and kidneys were immediately harvested gene expression or histological analyses. All protocols employing mice were conducted in accordance the principles and guidance of the University of Utah Institutional Animal Care and Committee.

Measurement of biochemical parameters

Urine samples were centrifuged for 5 minutes at 10,000 rpm. Blood samples from anesthetized mice were collected by puncturing the vena cava using a 1-ml insulin syringe containing 50 µl of 1 mM EDTA in the absence of protease inhibitors. Urine and plasma albumin was determined using a murine microalbuminuria enzyme-linked immunosorbent assay kit (Cat# 1011, EXOCELL). Plasma triglyceride level was determined using a LabAssay Triglyceride ELISA Kit (Cat#290-63701, WAKO). Urine and plasma levels of urea were measured by Urea Nitrogen Direct kit (Cat# 0580-250, Stanbio Laboratory,), and urine and plasma levels of creatinine were measured by Creatinine Liquicolor kit (Cat#0420-250, Stanbio Laboratory).

Morphological Studies

Under anesthesia, kidneys were removed and fixed with 4% paraformaldehyde. The tissues were subsequently embedded in paraffin and 4-µm sections were cut and stained with periodic acid Schiff (PAS). Glomerular sclerosis was assessed as follows using a semiquantitative score: grade 0, normal appearance; grade I, involvement of up to 25% of the glomerulus; grade II, involvement of 25 to 50% of the glomerulus; grade III, involvement of 50 to 75% of the glomerulus; grade IV, involvement of 75 to 100% of the glomerulus. A glomerulosclerosis index (GSI) was calculated by multiplying the number of glomeruli with a sclerosis score of I by one, the number with a score of II by two, III by three, and IV by four. These values were summed and divided by the number of glomeruli assessed, including those with a sclerosis score of zero. The SI for each kidney specimen was a sum of the points from 30 glomeruli. Tubulointerstitial injury (defined as tubular atrophy, dilatation, thickening of the basement membrane, protein cast) by semiquantitative analysis. Thirty cortical fields from each animal were examined at ×200 magnification and graded according to a scale of 0 to 4: 0, no tubulointerstitial injury 1, <25% of the tubulointerstitium injured; 2, 25% to 50% of the tubulointerstitium injured; 3, 51% to 75% of the tubulointerstitium injured; and 4, 76% to 100% of the tubulointerstitium injured. All sections were examined in blind manner.

Immunohistochemistry

Immunohistochemical staining was performed. Anti-WT1 antibody was purchased from Dako (Mob437, Dako).

qRT-PCR

Total RNA was isolated using TRIzol (Invitrogen, Carlsbad, Calif.), and first-strand cDNAs were synthesized from 2 µg of total RNA in 20 ml reaction using SuperScript (Invitrogen). The first strand cDNAs served as the template for quantitative PCR performed in Applied Biosystems 7900 Real Time PCR System using SYBR green PCR reagent (Applied Biosystems, Foster City, Calif., USA). The amplification was carried out for 40 cycles with conditions of 15-s denaturation at 95° C. The sequence of oligonucleotides used for qPCR (RT-PCR) is listed as follows: GAPDH sense: 5'-GTC TTCACTACCATGGAGAAGG-3' and antisense: 5'-TCATGGATGACCTTGGCC AG-3'; Fibronectin (FN) sense: 5'-CGTGGAGCAAGAAGGACAA-3' and antisense: 5'-GTGAGTCTGCGGTTGGTAAA-3'; SMAα sense: 5'-CCCTGAAGAGCATCC GACA-3' and antisense: 5'-CCAGAGTCCAGCACAATACC-3'; TGF-β sense: 5'-TAC GCCTGAGTGGCTGTCTT-3' and antisense: 5'-CGTGGAGTTTGTTATCTTTGCT-3'; ZO-1 sense: 5'-GCGCGGAGAGAGACAAGA-3' and antisense: 5'-CTGGCCCTC CTTTTAACACA-3'; p47$^{phox}$ sense: 5'-CACTCCCTTTGCTTCCATCT-3' and antisense: 5'-AT-GTTGCTATCCCAGCCAGT-3'; gp91$^{phox}$ sense: 5'-CCGT-ATTGT GGGAGACTGGA-3' and antisense: 5'-CTT-GAGAATGGAGGCAAAGG-3'; Desmin sense: 5'-GTGGATGCAGCCACTCTAGC-3' and antisense: 5'-TTAGCCGCGATG GTCCATAC-3; TNF-α sense: 5'-TC-CCCAAAGGGATGAGAAG-3' and antisense: 5'-CACT-TGGTGGTTTGCTACGA-3'; IL-1β sense: 5'- ACTGT-GAAATGCCACTTT TG-3' and antisense: 5'-TGTTGATGTGCTGCTGTGAG-3'; MCP-1 sense: 5'-GCT CTCTCTTCCTCCACCAC-3' and antisense: 5'-ACAGCTTCTTTGGGACACCT-3'. Collagen type III sense: 5'-AGGCAACAGTGGTTCTCCTG-3' and reverse 5'-GAC CTCGTGCTCCAGTTAGC-3'.

Immunoblotting

The kidney lysates were stored at −80° C. until assayed. Protein concentrations were determined using Coomassie reagent. An equal amount of the whole tissue protein was denatured at 100° C. for 10 min, separated by SDS-PAGE, and transferred onto nitrocellulose membranes. The blots were blocked overnight with 5% nonfat dry milk in Tris-buffered saline (TBS), followed by incubation for 1 h primary antibody. The blots were washed with TBS followed by incubation with horseradish peroxidase-conjugated secondary antibody. Immune complexes were detected using ECL methods. The immunoreactive bands were quantified using the Gel and Graph Digitizing System (Silk Scientific, Tustin, Calif.).

Measurement of Thiobarbituric Acid-Reactive Substances

The measurement of thiobarbituric acid-reactive substances (TBARS) in the mouse kidney was based on the formation of malondialdehyde (MDA) by using a commercially available TBARS Assay kit (catalog no. 10009055, Cayman Chemical) according to the manufacturer's instructions.

Statistical Analysis

All values are represented as means±SE. Data were analyzed using unpaired t-test or ANOVA followed by a Bonferroni posttest. Differences were considered to be significant when $P<0.05$.

Example 2

Figure 8A:
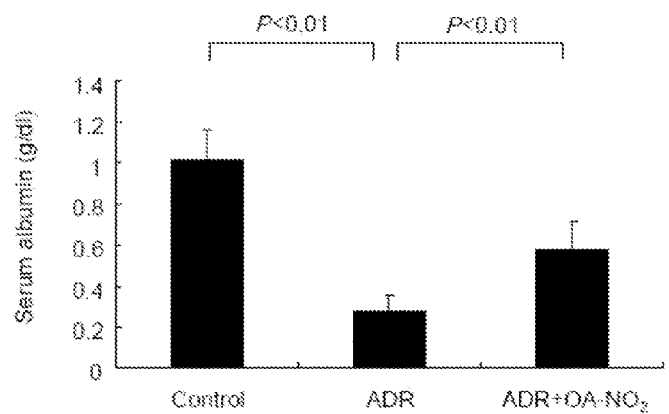
FIGS. 8a-8b. Nitrated fatty acid OA-NO$_2$ ameliorates hypoalbuminemia and ascites in ADR nephropathy.
Figure 8B:
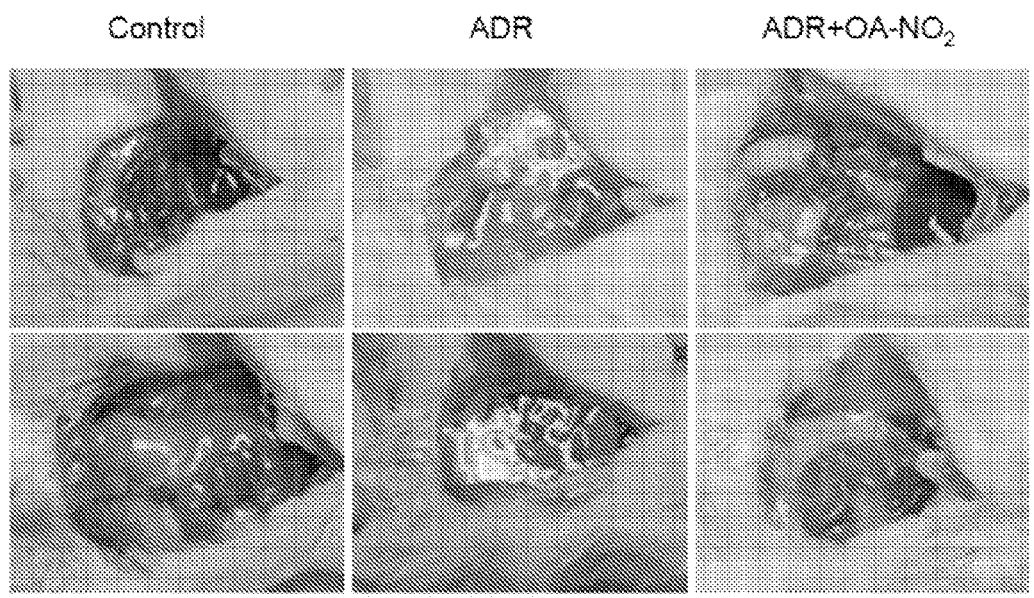

OA-NO$_2$ Attenuates Albuminuria and Renal Dysfunction in Managing Chemotherapy-Related Toxicity BALB/c mice were administered vehicle, ADR, or ADR in combination of OA-NO$_2$; OA-NO$_2$ was delivered via osmotic mini-pump 2 days prior to ADR injection. At day 5 after ADR injection, albuminuria was most evident in ADR group (508.89±48.52 µg/24 h) as compared with control group (33.39±3.50 µg/24 h), and was attenuated in ADR+OA-NO$_2$ group (342.40±33.26 µg/24 h). These changes were observed at day 3 and maintained at day 7. At day 7, plasma albumin was significantly reduced in the ADR group (0.28±0.08 g/dl) as compared with control group (1.01±0.15 g/dl) and was significantly restored in ADR+OA-NO$_2$ group, the decrease of plasma albumin levels were significantly attenuated (0.58±0.13 g/dl), as shown in FIG. 8A. Ninety percent of ADR mice had severe ascites at sacrifice contrasting to only 20% of ADR+OA-NO$_2$ mice having mild ascites, as shown in FIG. 8B.

Figure 9A:
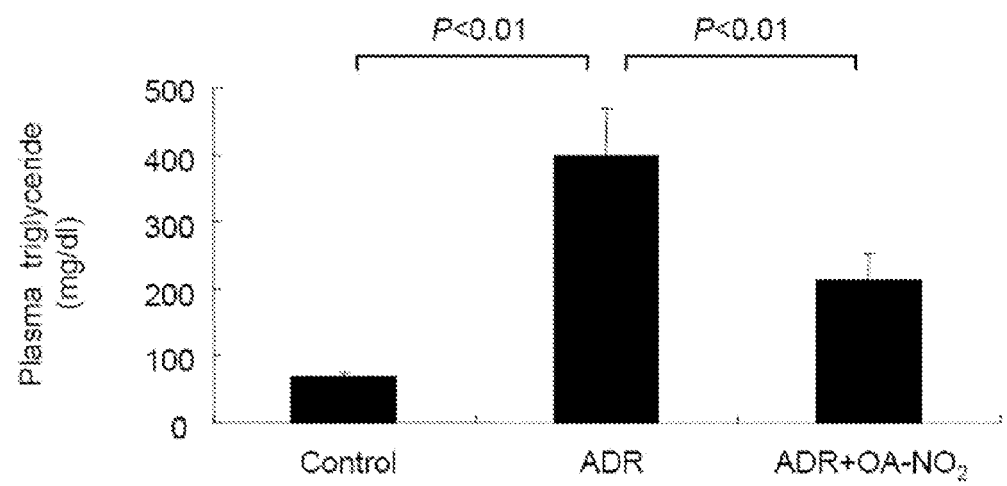
FIGS. 9a-9c. Nitrated fatty acid OA-NO$_2$ ameliorates hypertriglyceridemia and renal dysfunction in ADR nephropathy.
Figure 9B:
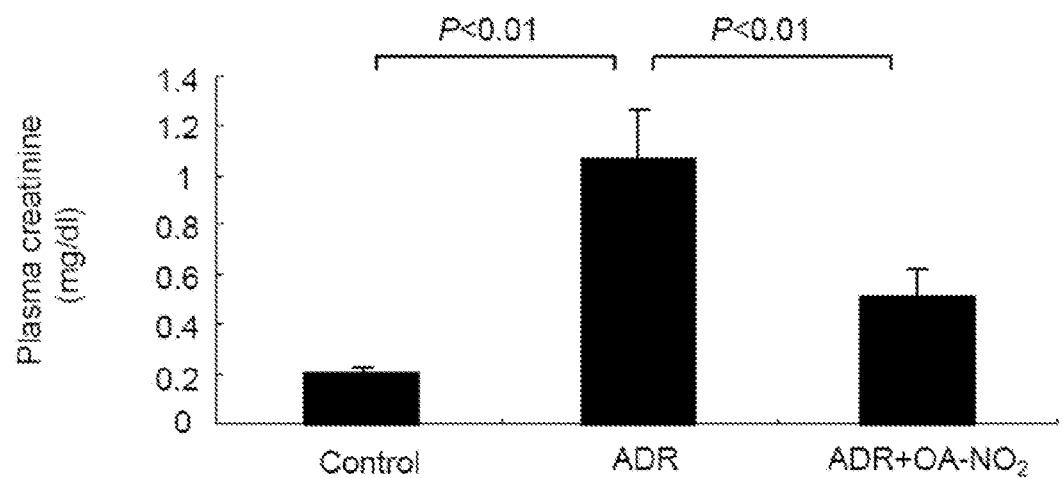
Figure 9C:
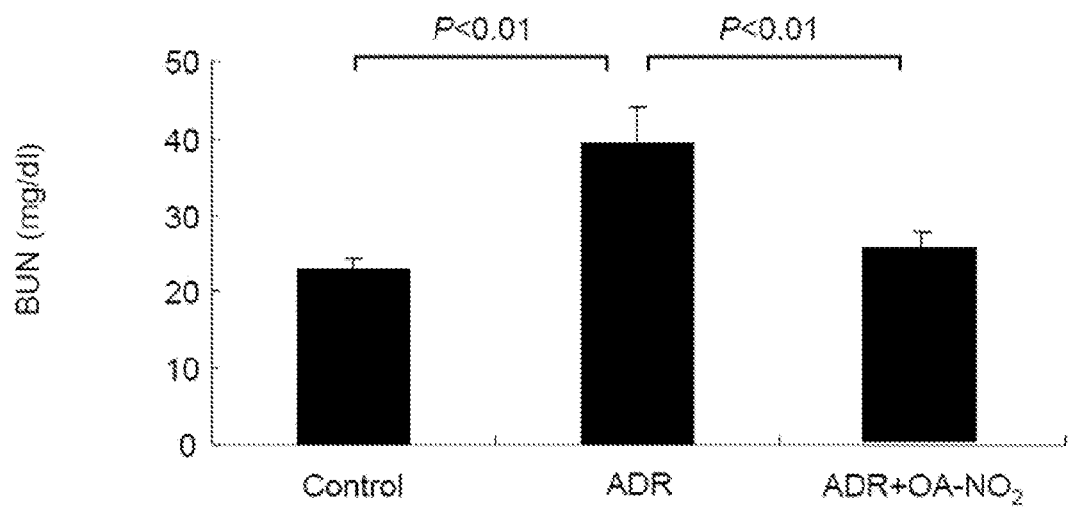
Figure 10A:
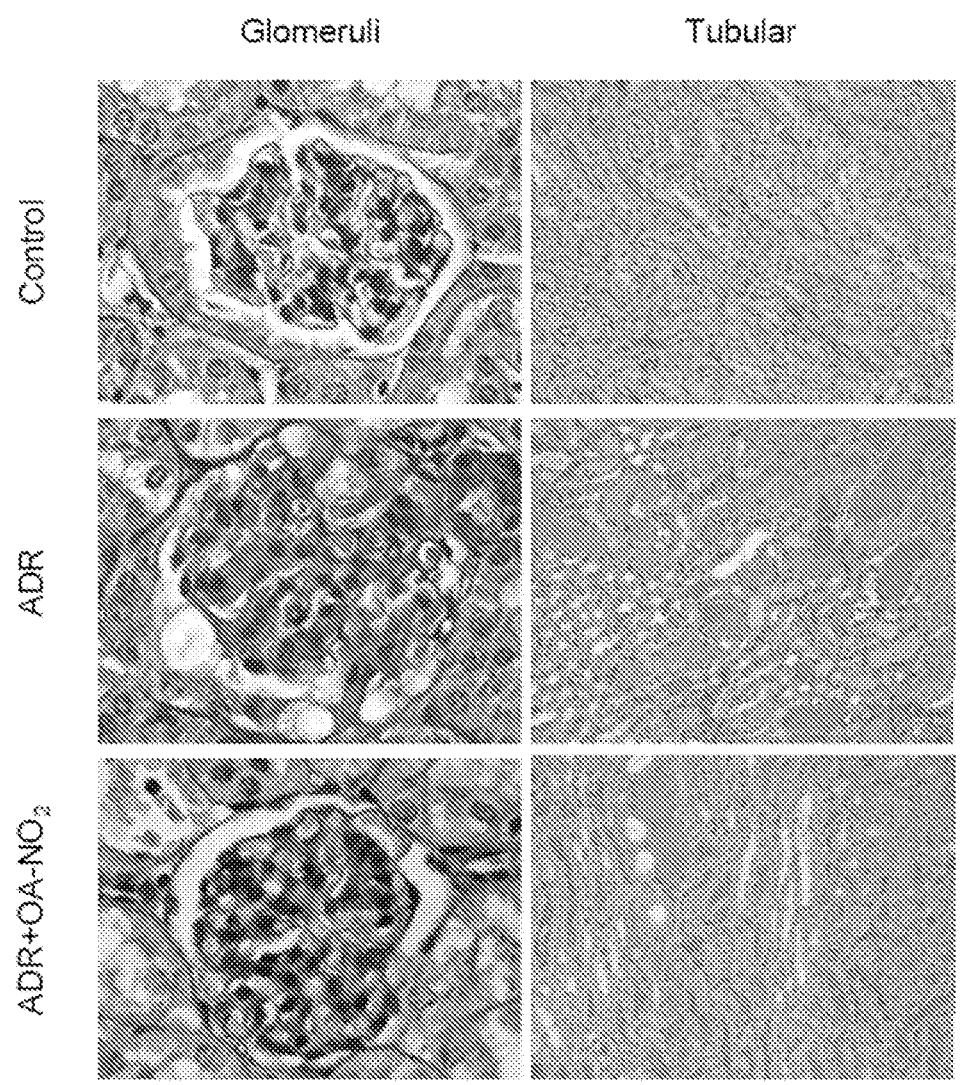
FIGS. 10a-10c. Nitrated fatty acid OA-NO$_2$ ameliorates glomerulosclerosis and tubulointerstitial lesion in ADR nephropathy.
Figure 10B:
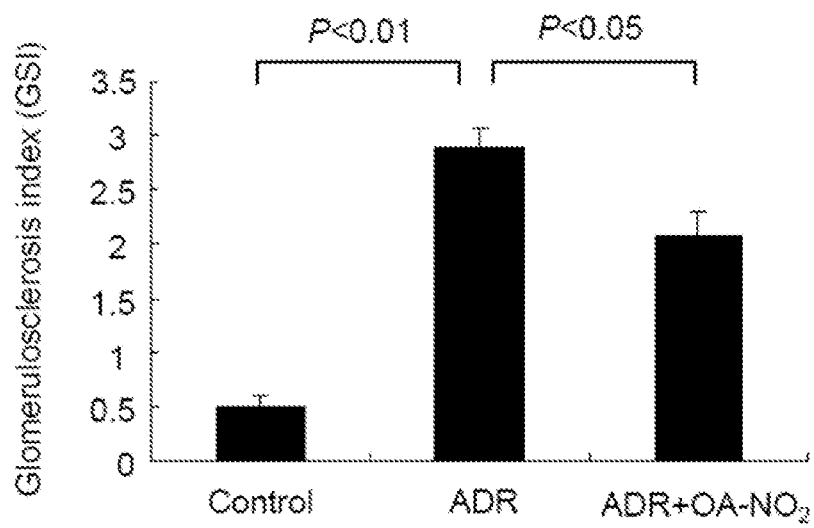
Figure 10C:
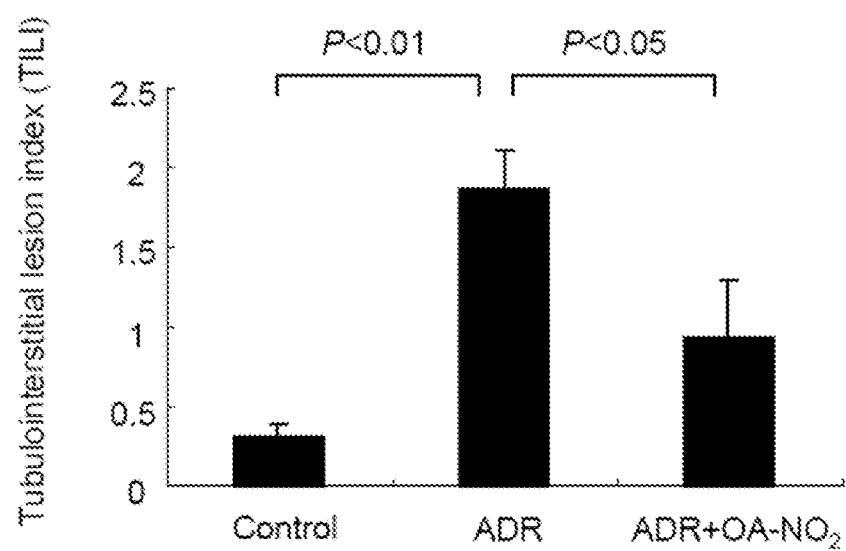

ADR mice developed severe hyperlipidemia (plasma triglyceride: 396.18±70.94 mg/dl) that was less in ADR+OA-NO$_2$ group (plasma triglyceride: 212.70±39.22 mg/dl) (FIG. 3A). Plasma creatinine and BUN were determined to reflect renal function. ADR mice had elevated plasma creatinine and BUN, both of which were significantly attenuated in ADR+OA-NO$_2$ group, as shown in FIGS. 9B-9C.

Example 3

OA-NO$_2$ Attenuates Glomerular Injury and Renal Fibrosis in Managing Chemotherapy-Related Toxicity To correlate the reduction of albuminuria to glomerular structure, the effect of drug treatments on glomerulosclerosis was assessed by periodic acid-Schiff (PAS) staining. Being consistent with the data on albuminuria, the ADR mice showed marked glomerulosclerosis as evidenced by mesangial expansion and increased accumulation of extracellular matrix (ECM) in the mesangium, as shown in FIG. 8A. A semiquantitative glomerulosclerotic index of kidney sections confirmed the histological data. The ADR mice showed the highest score, and OA-NO$_2$ treatment led to a marked reduction in the index (P<0.05), as shown in FIG. 8B.

Figure 11A:
FIGS. 11a-11f. Nitrated fatty acid OA-NO$_2$ preserves podocyte markers in ADR nephropathy.
Figure 11B:
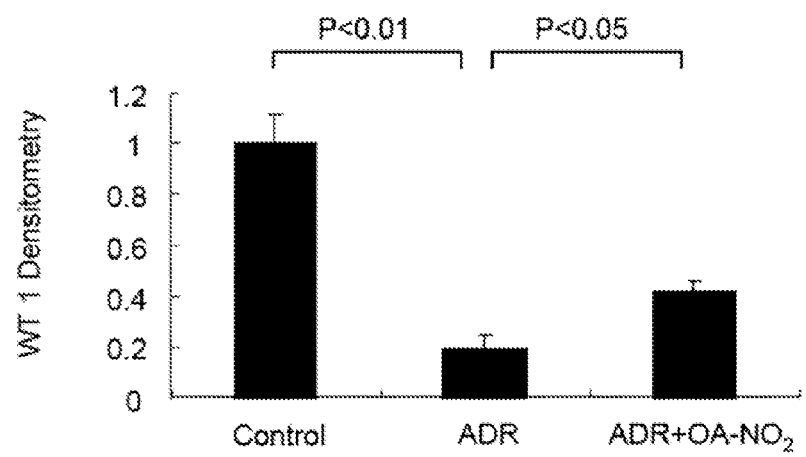
Figure 11C:
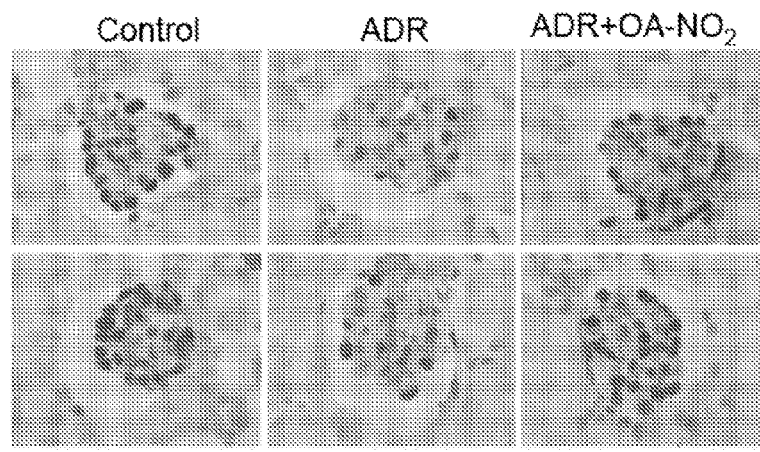
Figure 11D:
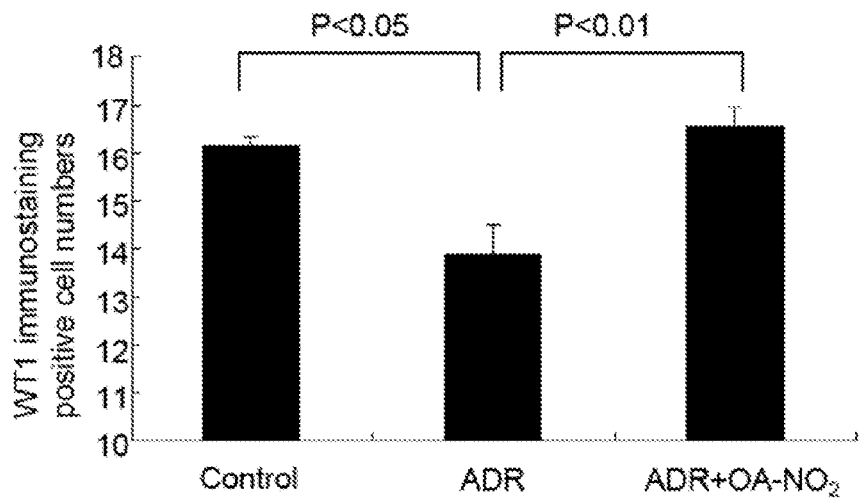
Figure 11E:
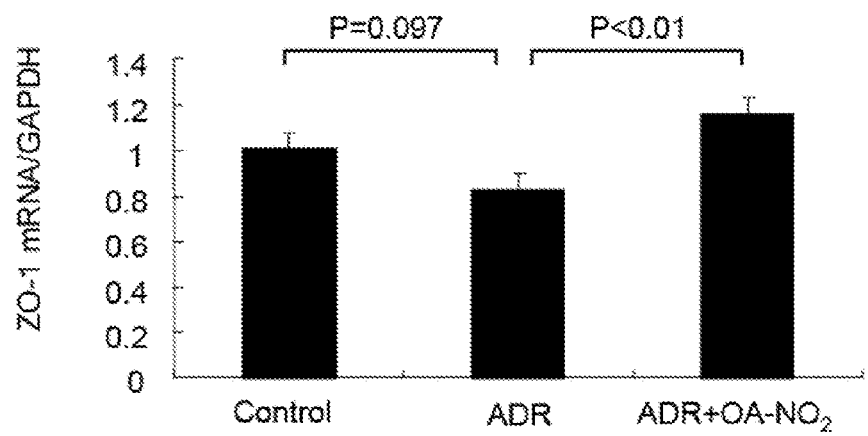
Figure 11F:
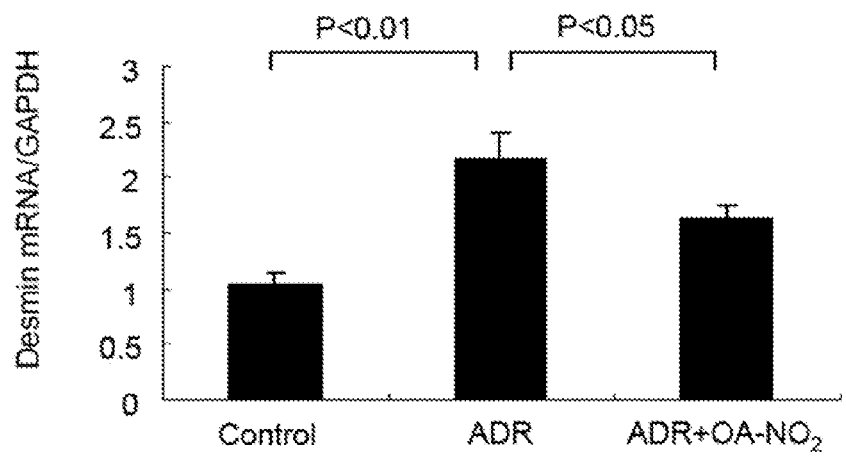

Because podocyte injury is an early and predominant pathologic feature of ADR model, expression of a number of podocyte markers was examined. WT1 is a pivotal transcription factor that is essential for the maintenance of the differentiated features of adult podocytes. As illustrated in FIGS. 11A&11B, immunoblotting revealed a marked reduction of WT1 after ADR injury compared with controls, OA-NO$_2$ pretreatment prevented the down-regulation of WT1 in the ADR mice (P<0.05). The number of podocytes was semi-quantitatively analyzed by immunohistochemical analysis of WT-1. The number of WT1-positive cells was reduced in the ADR group and was partially restored in the ADR+OA-NO$_2$ group, as shown in FIGS. 11C&11D. qRT-PCR was performed to examine mRNA expression of Zonula occludens-1 (ZO-1) and desmin. Renal ZO-1 mRNA exhibited a trend of reduction in the ADR group as compared with the control group and a significant elevation in the ADR+OA-NO$_2$ group, as shown in FIG. 11E. Desmin mRNA was up-regulated in the ADR mice, and treatment with OA-NO$_2$ prevented this increase, as shown in FIG. 11F.

Figure 12A:
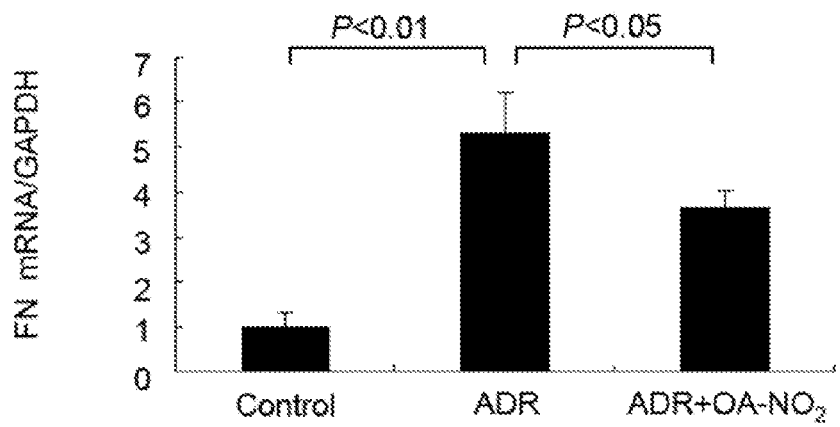
FIGS. 12a-12h. Nitrated fatty acid OA-NO$_2$ hampers renal fibrosis in ADR nephropathy.
Figure 12B:
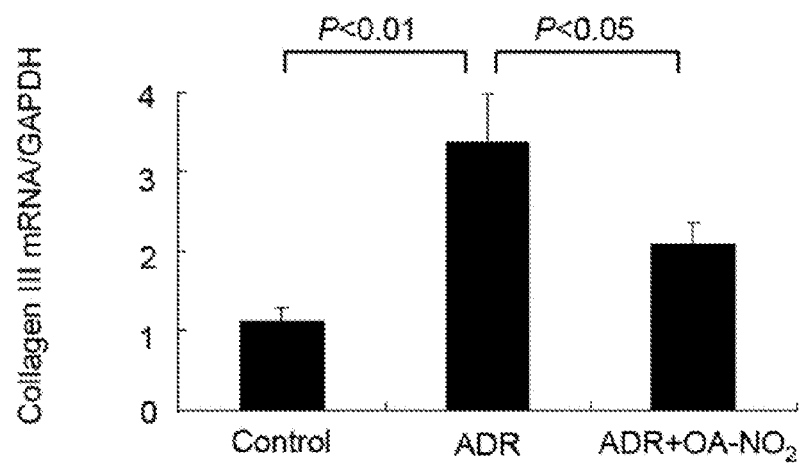
Figure 12C:
Figure 12D:
Figure 12E:
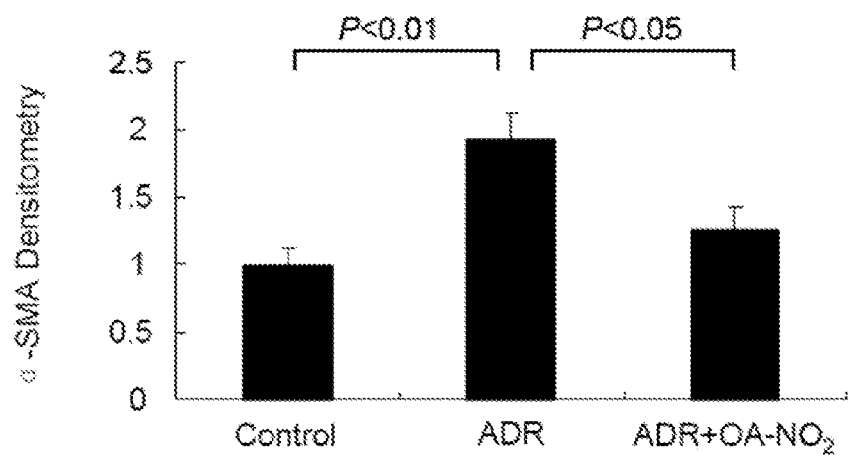
Figure 12F:
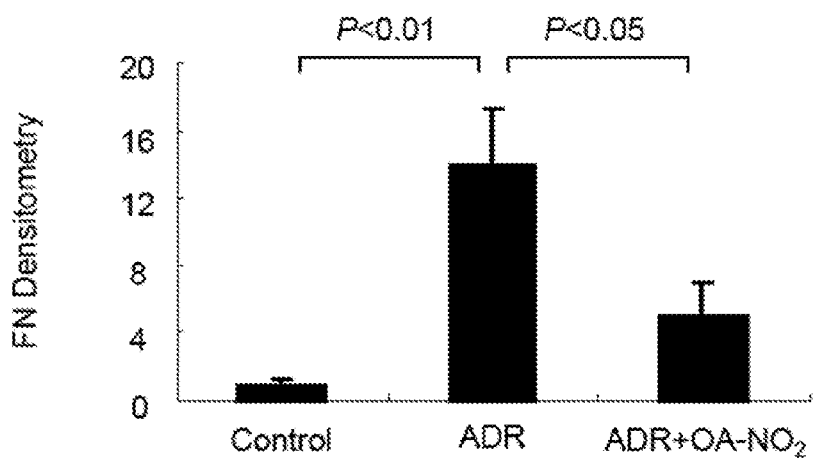
Figure 12G:
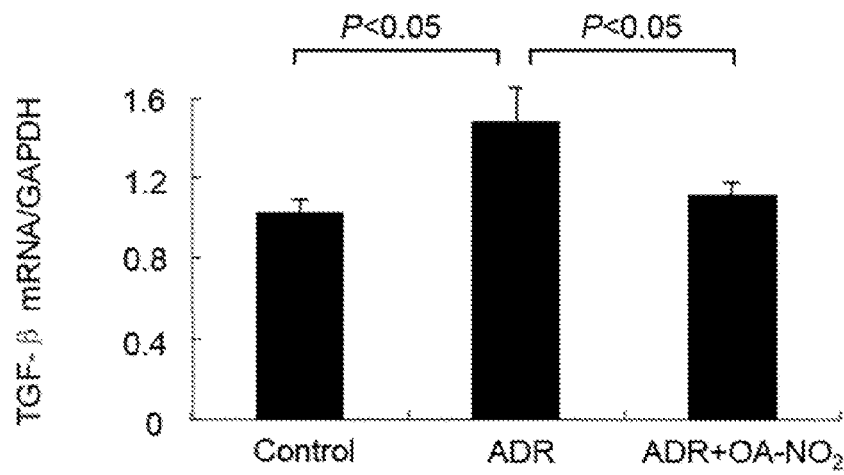
Figure 12H:
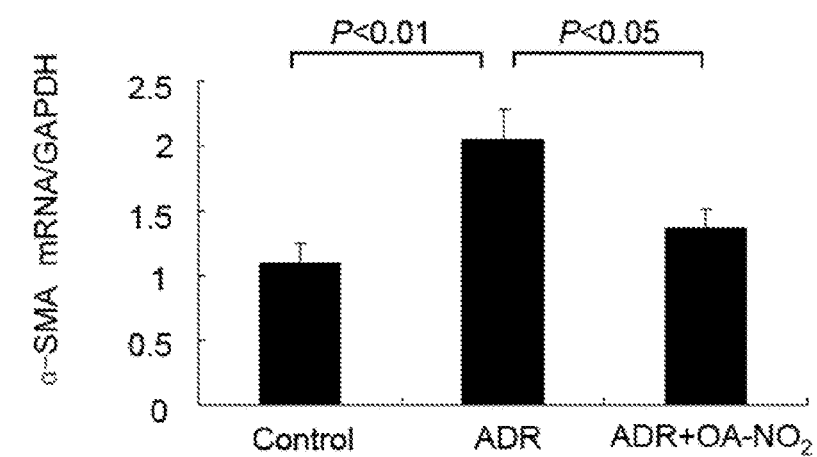

Renal fibrosis was examined by determining the expression of α-SMA and fibronectin (FN) and TGF-β in the kidney. As shown in FIGS. 12A-12, ADR mice showed marked increases in α-SMA and fibronectin (FN) expression at the mRNA levels relative to the control by real-time PCR (FIGS. 12A&12B), and Western blotting revealed marked up-regulation of α-SMA and FN (FIGS. 12C&12D). The densitometric values of these two proteins are shown in FIGS. 12E&12F. OA-NO$_2$ treatment prevented the up-regulation of α-SMA and FN in the ADR mice (P<0.05). In addition, the mRNA expression of several other fibrosis/sclerosis-related genes in the kidney was up-regulated in the ADR mice, including TGF-β (FIG. 12G), and collagen III (FIG. 12H). OA-NO$_2$ treatment induced a dramatic suppression of these genes in the kidney (P<0.05). These data are consistent with the antisclerotic effect of OA-NO$_2$ treatment.

Example 4

Figure 13A:
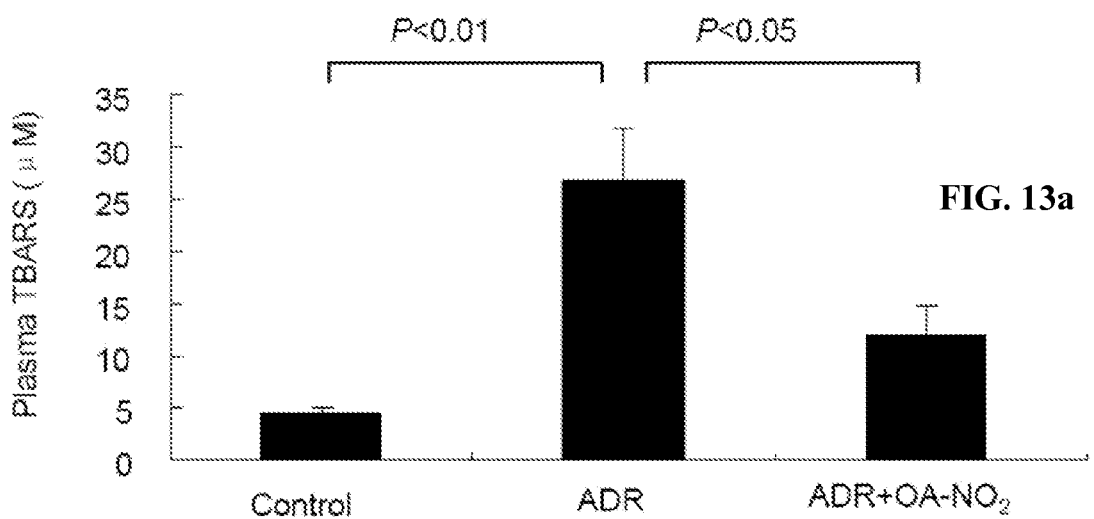
FIGS. 13a-13c. Effect of nitrated fatty acid OA-NO$_2$ on TBARS levels.
Figure 13B:
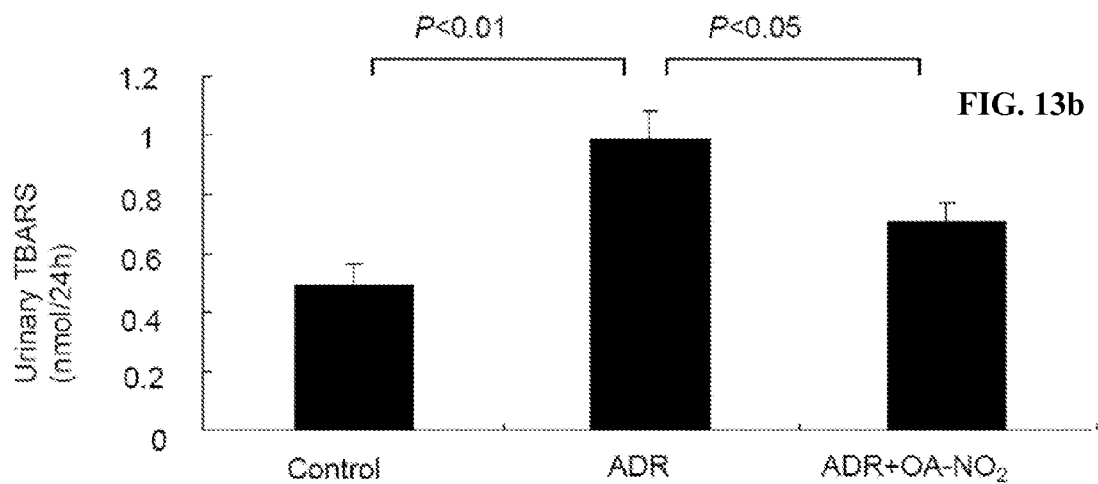
Figure 13C:
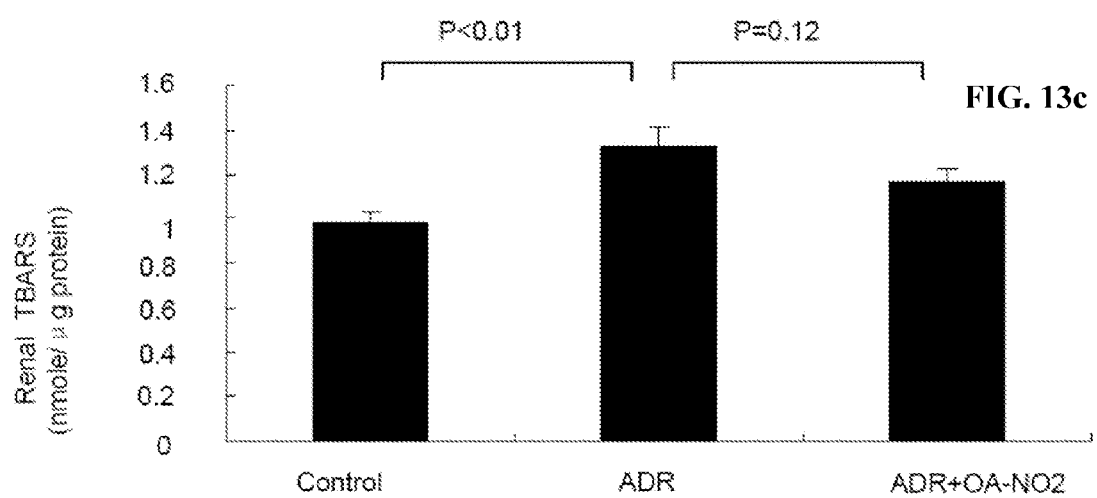
Figure 14A:
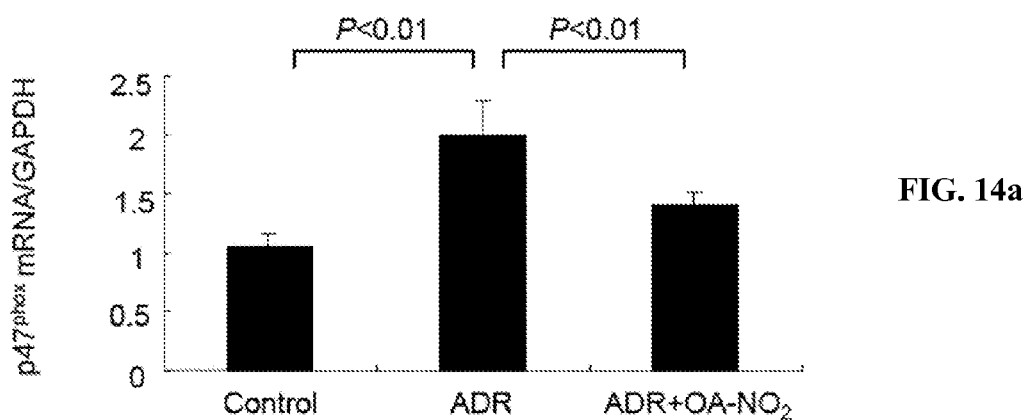
FIGS. 14a-14d. Effect of nitrated fatty acid OA-NO$_2$ on renal mRNA expression of NADPH oxidase subunits.
Figure 14B:
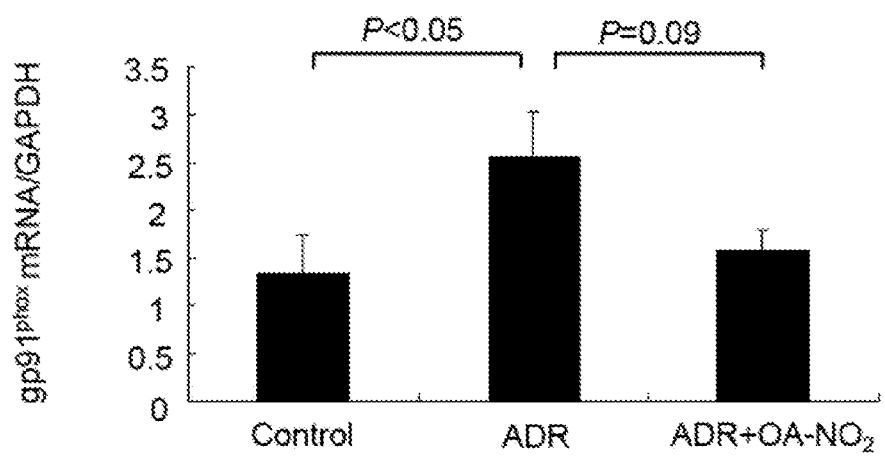
Figure 14C:
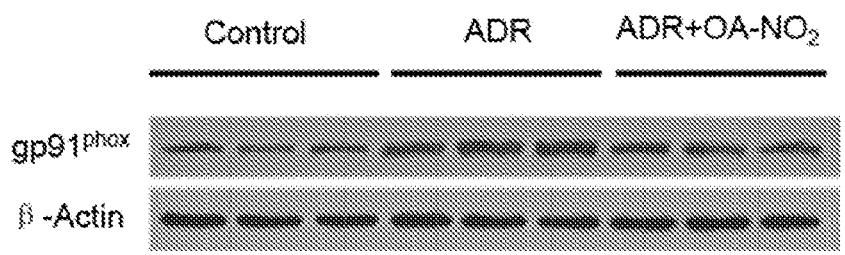
Figure 14D:
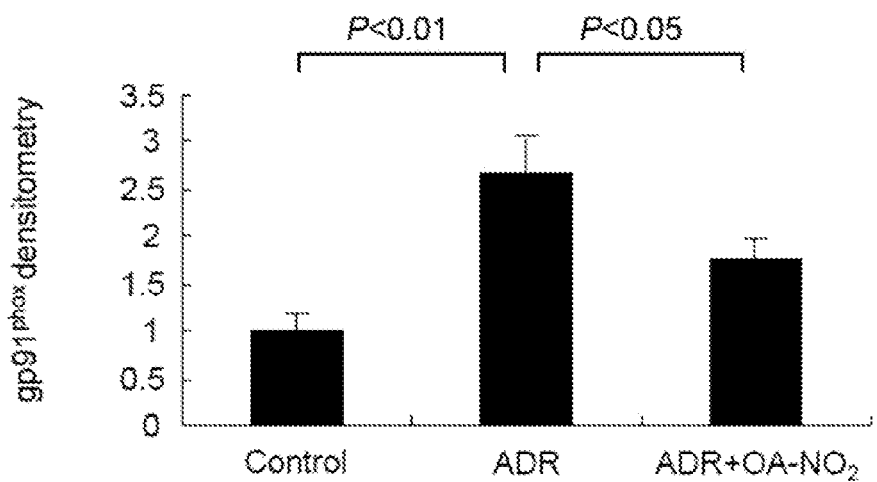

OA-NO$_2$ Hampers Renal Oxidative Stress in Managing Chemotherapy-Related Toxicity Among many possible pathogenic factors, oxidative stress has emerged as an important pathogenic factor in the development of ADR nephropathy. To investigate whether OA-NO$_2$ had antioxidative effect in ADR mice, plasma and urinary levels of thiobarbituric acid reactive substances (TBARS) was analyzed, which is a reliable product of lipid oxidation. As a result, the ADR group showed a marked increase in plasma (FIG. 13A) urinary (FIG. 13B) and kidney (FIG. 13C) TBARS as compared to the control group. Treatment with OA-NO$_2$ markedly attenuated ADR-induced increase in plasma and urinary TBARS as compared to ADR mice, as shown in FIGS. 13A&13B. There was a trend of reduction of TBARS levels in response to OA-NO2 treatment but this did not reach a statistical significance. NAD(P)H oxidase is an important source of ROS generation in various pathological conditions. Renal expression of major subunits of NAD(P)H oxidase was examined. As shown in FIGS. 14A&B, renal mRNA expression of p47$^{phox}$ and gp91$^{phox}$ was significantly increased in ADR mice as compared with the control group and the increase was less in the ADR+OA-NO$_2$ group (P<0.05). The change in gp91$^{phox}$ was further confirmed at the protein level (P<0.01; FIGS. 14C&14D).

Example 5

OA-NO$_2$ Hampers Renal Inflammation in Managing Chemotherapy-Related Toxicity

Figure 15A:
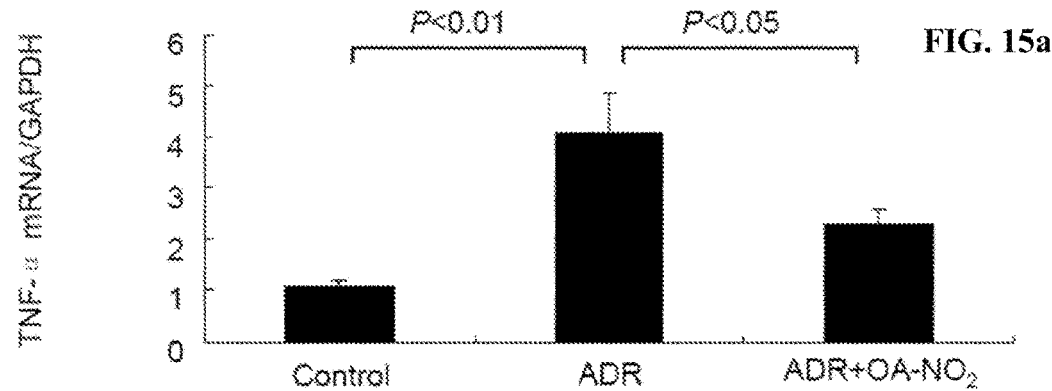
FIGS. 15a-15c. Nitrated fatty acid OA-NO$_2$ attenuates renal inflammation in ADR nephropathy. qRT-PCR was performed to determine renal mRNA expression in bar graphs for TNF-α (FIG. 15a), IL-β (FIG. 15b) and MCP-1 (FIG. 15c). Control: n=8; ADR: n=18; ADR+OA-NO$_2$: n=16. Values are means±SE.
Figure 15B:
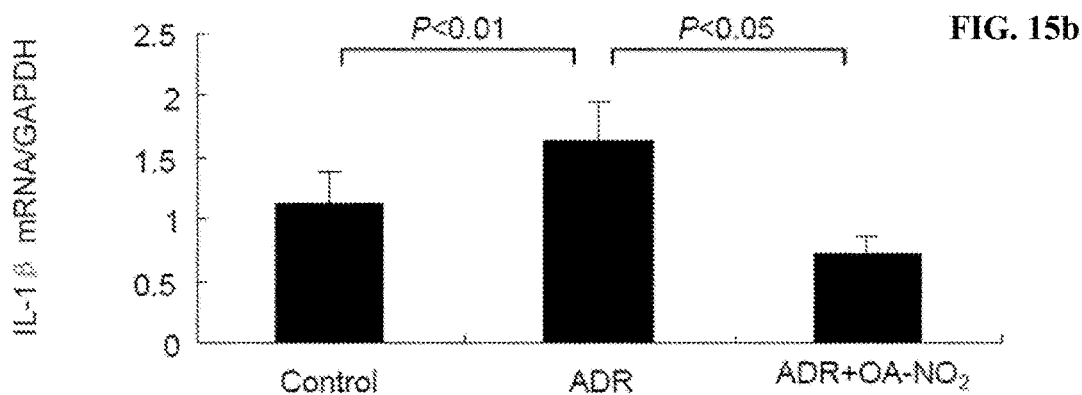
Figure 15C:
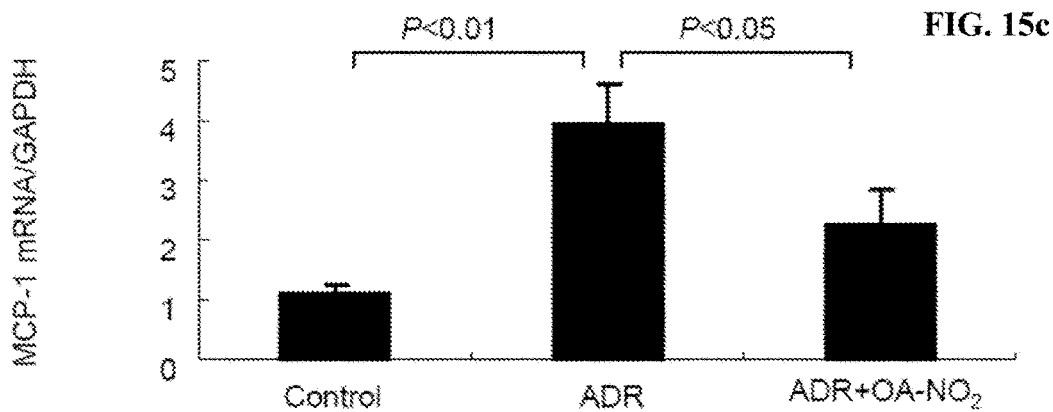

ADR induces proinflammatory response in the kidney, releasing cytokines and chemokines responsible for subsequent kidney injury. To examine whether OA-NO$_2$ could reduce inflammation, qRT-PCR analysis of TNF-α, IL-1β, and MCP-1 was performed. The renal expression of these proinflammatory mediators was in induce din parallel in ADR mice and the inductions were all suppressed by OA-NO$_2$ as shown in FIGS. 15A-15C.

Example 6

Prophetic Examples

A 50 year old is diagnosed with invasive lung cancer. The cancer is visualized either clinically or radiographically, and the patient undergoes pretreatment or posttreatment with a nitrated lipid and then exposed to chemotherapy or radiation. The chemotherapy may include a chemical agent of at least one of the following: alkylating agents, anti-metabolites, alkaloids and terpenes, topoisomerase inhibitors, antibiotics, monoclonal antibodies, tyrosine kinase inhibitors, nanoparticles, hormones, contrast agents, NSAIDS, COX-2 inhibitors, ACE inhibitors, ARBs, and lithium. Alternatively, patient is exposed to physical agent including at least one of the following: ionizing radiation, proton therapy, electro-chemotherapy, or laser radiation. After chemotherapy or radiation, the nitrated lipid lessens a side effect of the chemotherapy or radiation including at least one of: organ system damage, nausea, vomiting, and hair loss. The patient experiences an improved clinical outcome.

In the above example, the patient's organ systems including at least one of: the urinary system, the digestive system, the nervous system, the auditory system, the circulatory system, the endocrine system, the excretory system, the skeletal system, the respiratory system, the reproductive system, the muscular system, the lymphatic system, immune system, integumentary system, and the integumentary system. The tissues are injected by radiographic guidance or direct visualization during mediastinoscopy or surgery. Following injection, it is noticed that there may be less side effects of the chemotherapy or radiation. Nitrated lipid administration may be repeated in intervals as necessary.

The mechanism of action of the nitrated lipid on the chemical agent as to relieve the side effects is dependent on the chemical agent's mode of action in chemotherapy. Alkylating agents are so named because of their ability to alkylate many nucleophilic functional groups under conditions present in cells and impair cell function by forming covalent bonds with the amino, carboxyl, sulfhydryl, and phosphate groups in biologically important molecules, such as DNA. Nitrated lipids may decrease side effects of alkylating agents by attenuating plasma level of MPO (marker of neutrophil infiltration), attenuating expression of NADPH oxidase subunits $p47^{phox}$ and $gp91^{phox}$ (major superoxide generating enzyme), attenuating thiobarbituric acid-reactive substances (TBARS, index of oxidative stress), and attenuating activity of caspase (index of apoptosis).

Anti-metabolites masquerade as purines (azathioprine, mercaptopurine) or pyrimidines—which become the building-blocks of DNA. Anti-metabolites prevent these substances from becoming incorporated into DNA during the "S" phase (of the cell cycle), stopping normal development and division. Anti-metabolites also affect RNA synthesis and due to their efficiency, Anti-metabolites are the most widely used cytostatics. Nitrated lipids may decrease side effects of alkylating agents by inhibiting NF-κB, preserve expression of WT1 proteins, prevent downregulation of WT1 proteins, reverse the mRNA reduction of epithelial marker ZO-1, inhibit production of proinflammatory cytokines Tumor necrosis factor (TNF-α), Interleukin 1 (IL-1β) and monocyte chemotactic protein-1 (MCP-1), attenuate ADR-induced up-regulation of NADPH oxidase subunit $gp91^{phox}$ and $p47^{phox}$ at both mRNA and protein levels. Alkaloids are derived from plants and block cell division by preventing microtubule function, bind to specific sites on tubulin, inhibiting the assembly of tubulin into microtubules. Topoisomerases are essential enzymes that maintain the topology of DNA Inhibition of type I or type II topoisomerases interferes with both transcription and replication of DNA by upsetting proper DNA supercoiling. Nitrated lipids may decrease side effects of alkaloids and topoisomerases by inhibiting NF-κB, preserve expression of WT1 proteins, prevent downregulation of WT1 proteins, reverse the mRNA reduction of epithelial marker ZO-1, inhibit production of proinflammatory cytokines Tumor necrosis factor (TNF-α), Interleukin 1 (IL-1β), inducible nitric oxide synthase (iNOS), Cyclooxygenase-2 (COX-2), ICAM-1.VCAM-1, and monocyte chemotactic protein-1 (MCP-1), attenuate ADR-induced up-regulation of NADPH oxidase subunit $gp91^{phox}$ and $p47^{phox}$ at both mRNA and protein levels. Nitrated lipids may decrease side effects of alkaloids by inhibiting NF-κB, preserve expression of WT1 proteins, prevent downregulation of WT1 proteins, reverse the mRNA reduction of epithelial marker ZO-1, inhibit production of proinflammatory cytokines Tumor necrosis factor (TNF-α), Interleukin 1 (IL-1β) and monocyte chemotactic protein-1 (MCP-1), attenuate ADR-induced up-regulation of NADPH oxidase subunit $gp91^{phox}$ and $p47^{phox}$ at both mRNA and protein levels.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of treating renal system damage in a subject, comprising:
   administering to the subject an effective amount of a nitrated fatty acid,
   wherein the renal system damage is selected from the group consisting of distortion of the overall renal morphology, appearance of protein cast, oxidative stress, and apoptosis of organ cells; and
   wherein the nitrated fatty acid is 10-nitro oleic acid.

2. The method of claim 1, wherein the renal system damage is distortion of the overall renal morphology.

3. The method of claim 1, wherein the renal system damage is appearance of protein cast.

4. The method of claim 1, wherein the renal system damage is oxidative stress.

5. The method of claim 2, wherein the renal system damage is apoptosis of organ cells.

* * * * *

UNITED STATES PATENT AND TRADEMARK OFFICE
CERTIFICATE OF CORRECTION

PATENT NO. : 10,369,125 B2
APPLICATION NO. : 15/492732
DATED : August 6, 2019
INVENTOR(S) : Tianxin Yang It is certified that error appears in the above-identified patent and that said Letters Patent is hereby corrected as shown below:

In the Specification

Column 1 Line 20 delete "This invention was made with government support under Grant Numbers HL079453 and RO- DK 066592 awarded by the National Institutes of Health. The government has certain rights to this invention."

And replace it with:
--This invention was made with government support under grants R01 DK066592 and HL079453 awarded by the National Institutes of Health. The government has certain rights in this invention.--

Signed and Sealed this
Eighth Day of October, 2019

Andrei Iancu
*Director of the United States Patent and Trademark Office*